(12) United States Patent
Soutschek et al.

(10) Patent No.: US 6,274,307 B1
(45) Date of Patent: Aug. 14, 2001

(54) IMMUNOLOGICALLY ACTIVE PEPTIDES OR POLYPEPTIDES FROM THE PARVOVIRUS B19

(75) Inventors: Erwin Soutschek; Manfred Motz, both of München (DE)

(73) Assignee: MIKROGEN molekularbiologische Entwicklungs-GmbH, Munich (DE)

( * ) Notice: Subject to any disclaimer, the term of this patent is extended or adjusted under 35 U.S.C. 154(b) by 0 days.

(21) Appl. No.: 08/856,841

(22) Filed: May 15, 1997

Related U.S. Application Data

(63) Continuation of application No. 08/214,658, filed on Mar. 16, 1994, now abandoned, which is a continuation-in-part of application No. 07/917,096, filed on Aug. 4, 1992, now abandoned.

(30) Foreign Application Priority Data

Feb. 8, 1990 (DE) ................................................ 40 03 826
Feb. 8, 1991 (WO) .................................. PCT/DE91/00106

(51) Int. Cl.[7] ........................................................ C12Q 1/70
(52) U.S. Cl. ................................................ 435/5; 435/975
(58) Field of Search ............................. 435/5, 7.5, 7.92, 435/975

(56) References Cited

U.S. PATENT DOCUMENTS 5,508,186 * 4/1996 Young et al. ...................... 435/235.1
6,132,732 * 10/2000 Young et al. ............................ 435/5

FOREIGN PATENT DOCUMENTS

9013567 * 11/1990 (WO) .

OTHER PUBLICATIONS

Cotmore et al (J. Virol. 60:548–557), 1986.*
Morinet et al (J. Gen. Virol. 70:3091–3097), 1989.*
Bryan et al (Arch. Pathol. Lab. Med. 111:1015–1023), 1987.*

Harlow et al Antibodies a Laboratory Manual pp. 322 and 558.*

Rayment et al. The Production of Human Papvovirus Capsid Proteins in *Escherichia coli* an Their Potential as Diagnostic Reagents J. General Virology 71, 2665–2672 (1990.*

Moniet et al. Development of an IgM Capture Test Using Labelled Fusion–Proteinas Antigen for Diagnosis of B19 Human Papvovirus Infections Behring Institute Mitt. 85, 28–34, 1990.*

Sommer, et al., *Nucleic Acids Research*, vol. 17, No. 16, 1989, p. 6749.*

Koch et al. *Journal of Clinical Microbiology*, Jan. 1990, vol. 28, No. 1, pp. 65–69.*

* cited by examiner

*Primary Examiner*—Mary E. Mosher
(74) *Attorney, Agent, or Firm*—Norris McLaughlin & Marcus

(57) ABSTRACT

Immunologically active peptides or polypeptides with a partial amino-acid sequence of the capsid proteins VP1 and VP2 of parvovirus B19 which permit tests to be carried out at low cost, sensitively and specifically for the determination of antibodies against human parvovirus B19 are made available. Short peptide sequences which, employed as antigen, serve to identify anti-B19 IgG-positive sera are identified. Furthermore, the production of these peptides using genetic engineering measures is disclosed. Other antigens which are produced by genetic engineering and which can be stably produced in a high yield in *E.coli* and subsequently purified therefrom are used as additional antigens for IgG detection. Finally, a set of antigens permits tests to be carried out to determine IgM antibodies against the virus. In addition, the components, produced by genetic engineering, of the surface proteins represent substances which can be used for prophylactic immunisation.

20 Claims, 12 Drawing Sheets

FIG. 1

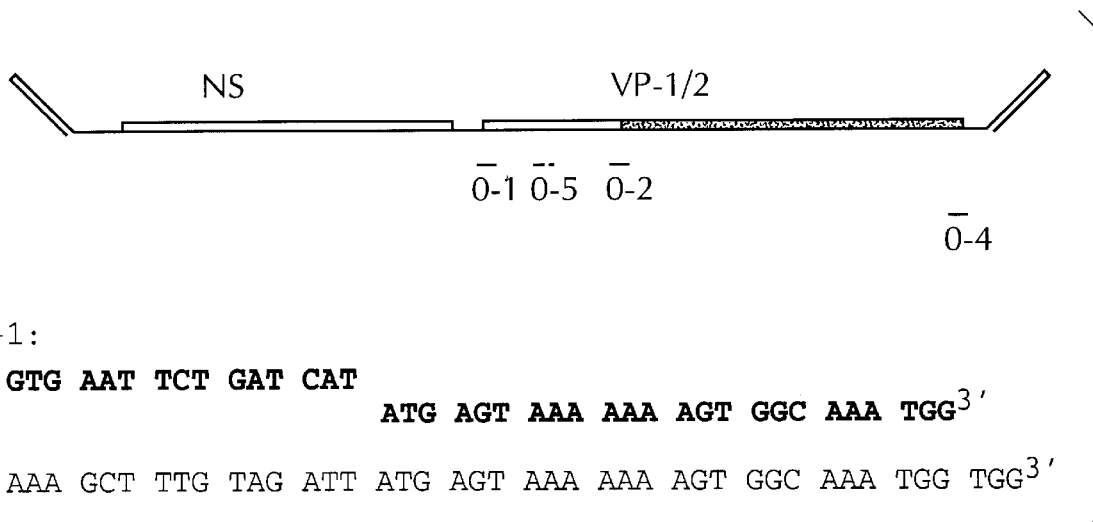

O-1:
5'GTG AAT TCT GAT CAT
             ATG AGT AAA AAA AGT GGC AAA TGG3'

5'AAA GCT TTG TAG ATT ATG AGT AAA AAA AGT GGC AAA TGG TGG3'

3'TTT CGA AAC ATC TAA TAC TCA TTT TTT TCA CCG TTT ACC ACC5'

O-2:
5'ATT CTG CAG AAG CCA GCA CTG GTG CAG GAG GGG GGG GCA3'

3'TAA GAC GTC TTC CGT CGT GAC CAC GTC CTC CCC CCC CGT5'

3'C TTC GGT CGT GAC CAC GTC CTC CCC5'

O-3:
5'G AGG AAT TCT CTG ATC
             ATG ACT TCA GTT AAT TCT GCA GAA GCC3'

5'A GAA AAA TAC CCA AGC ATG ACT TCA GTT AAT TCT GCA GAA GCC3'

3'T CTT TTT ATG GGT TCG TAC TGA AGT CAA TTA AGA CGT CTT CGG3'

O-4:
5'TTG TAA ACA CTC CCC ACC GTG CCC TCA GCC AGG ATG CGT A3'

3'AAC ATT TGT GAG GGG TCC CAC GGG AGT CGG TCC TAC GCA T5'

3'GAG GGG TGG CAC GGG AGT CGG TCC T
                                        TC GAA GAG5'

O-5:
5'  G CTA CAA GCT GGG CCC CCG CAA AG3'    -------

5'GAG CTA CAA GCT GGG CCC CCG CAA AGT GCT GTT GAC AGT GCT3'

3'CAC GAT GTT CGA CCC GGG GGC GTT TCA CGA CAA CTG TCA CGA5'

FIG. 2-1

Met Ser Lys Lys Ser Gly Lys Trp Trp Glu Ser Asp Asp Lys Phe Ala Lys Ala Val Tyr Gln Gln Phe Val Glu
Phe Tyr Glu Lys Val Thr Gly Tyr Phe Asp Leu Phe Asp Leu Ile Gln Ile Leu Lys Asp His Tyr Asn Ile Ser Leu Asp
Asn Pro Leu Glu Asn Pro Ser Ser Leu Phe Asp Gln Leu Val Ala Arg Ile Lys Asn Leu Lys Asn Ser Ser Pro Asp
Leu Tyr Ser His His Phe Gln Ser His Gly Leu Ser Asp Leu Ser Asp Leu Ser Pro His Ala Leu Ser Val Ser Ser His Ala
Glu Pro Arg Gly Glu Asn Ala Val Leu Ser Ser Glu Gln Leu Asp Leu Lys Pro Gly Gln Val Ser Val Gln Leu Pro
Gly Thr Asn Tyr Val Gly Pro Gly Asn Glu Leu Gln Ala Gly Pro Gln Ser Ala Val Asp Ser Ala Ala Arg
Ile His Asp Phe Arg Tyr Ser Gln Leu Ala Lys Leu Gly Ile Asn Pro Tyr Thr Thr His Trp Val Ala Asp Glu
Glu Leu Leu Lys Asn Ile Lys Asn Glu Thr Gly Phe Gln Ala Gln Val Val Lys Asp Tyr Phe Thr Leu Lys Gly
Ala Ala Pro Val Ala His Phe Gln Gln Gly Ser Leu Pro Val Pro Ala Tyr Asn Ala Ser Glu Lys Tyr Pro
Ser

FIG. 2-2

Glutathione-S-Transferase His Met Ser Lys Lys Ser Gly Lys Trp Trp Glu Ser Asp Asp Lys Phe Ala Lys Ala
Val Tyr Gln Gln Phe Val Glu Phe Tyr Glu Lys Val Thr Gly Tyr Phe Asp Leu Phe Asp Leu Ile Gln Ile Leu Lys Asp
His Tyr Asn Ile Ser Leu Asp Asn Pro Leu Glu Asn Pro Ser Ser Leu Phe Asp Gln Leu Val Ala Arg Ile Lys Asn
Asn Leu Lys Asn Ser Ser Pro Asp Leu Tyr Ser His His Phe Gln Ser His Gly Leu Ser Asp Leu Ser Asp Leu Ser Pro His Ala
Leu Ser Val Ser Ser His Ala Glu Pro Arg Gly Glu Asn Ala Val Leu Ser Ser Glu Gln Leu Asp Leu Lys Pro Gln
Gly Gln Val Ser Val Gln Leu Pro Gly Thr Asn Tyr Val Gly Pro Gly Asn Glu Leu Gln Ala Gly Pro Pro Tyr
Ser Ala Val Asp Ser Ala Ala Arg Ile His Asp Phe Arg Tyr Ser Gln Leu Ala Lys Leu Gly Ile Asn Pro Tyr
Thr His Trp Val Ala Asp Glu Glu Leu Leu Lys Asn Ile Lys Asn Glu Thr Gly Phe Gln Ala Gln Val Val Val
Lys Asp Tyr Phe Thr Leu Lys Gly Ala Ala Pro Glu Phe Ile Val Thr Asp

FIG. 2-3

Gly Ser Arg Arg Pro Asp His Met Ser Lys Lys Ser Gly Lys Trp Trp Glu Ser Asp Asp Lys Phe Ala Lys Ala
Val Tyr Gln Gln Phe Val Glu Phe Tyr Glu Lys Val Thr Gly Tyr Phe Asp Leu Phe Asp Leu Ile Gln Ile Leu Lys Asp
His Tyr Asn Ile Ser Leu Asp Asn Pro Leu Glu Asn Pro Ser Ser Leu Phe Asp Gln Leu Val Ala Arg Ile Lys Asn
Asn Leu Lys Asn Ser Ser Pro Asp Leu Tyr Ser His His Phe Gln Ser His Gly Leu Ser Asp Leu Ser Asp Leu Ser Pro His Ala
Leu Ser Val Ser Ser His Ala Glu Pro Arg Gly Glu Asn Ala Val Leu Ser Ser Glu Gln Leu Asp Leu Lys Pro Gln
Gly Gln Val Ser Val Gln Leu Pro Gly Thr Asn Tyr Val Gly Pro Gly Asn Glu Leu Gln Ala Gly Pro Pro Tyr
Ser Ala Val Gly Asp Pro Arg Glu Phe Ile Val Thr Asp

FIG. 2-4

```
Gly Ile Leu Ser Arg Arg Pro Asp His Met Ser Lys Ser Gly Lys Trp Trp Glu Ser Asp Asp Lys Phe Ala
Lys Ala Val Tyr Gln Gln Phe Val Glu Phe Tyr Glu Lys Val Thr Gly Leu Glu Leu Ile Gln Ile Leu
Lys Asp His Tyr Asn Ile Ser Leu Asp Asn Pro Ser Leu Asn Pro Ser Leu Phe Asp Ser Leu Val Ala Arg Ile
Lys Asn Asn Leu Lys Asn Ser Ser Pro Asp Leu Tyr Ser His His Gly Gln Leu Ser Glu Asp His Pro
His Ala Leu Ser Ser Ser Ser His Ala Glu Gly Gly Glu Asn Ala Val Leu Ser Glu Asp Leu His
Lys Pro Gly Gln Val Ser Val Gln Leu Pro Gly Thr Asn Tyr Val Gly Pro Gly Asn Gln Ala Gly Pro
Pro Gln Ser Ala Val Gly Asp Pro Leu Glu Pro Arg Val Pro Ser Asn Ser
```

FIG. 2-5

```
Gly Ser Arg Arg Pro Asp His Met Ser Lys Ser Gly Lys Trp Trp Glu Ser Asp Asp Lys Phe Ala Lys Ala
Val Tyr Gln Gln Phe Val Glu Phe Tyr Glu Lys Val Thr Gly Leu Glu Leu Ile Gln Ile Leu Leu Lys Asp
His Tyr Asn Ile Ser Leu Asp Asn Pro Ser Leu Asn Pro Ser Leu Phe Asp Ser Leu Val Ala Arg Ile Lys Asn
Asn Leu Lys Asn Ser Ser Pro Asp Leu Tyr Ser His His Gly Gln Leu Ser Glu Asp His Pro His Ala
Leu Ser Ser Ser Ser His Ala Glu Gly Gly Glu Asn Ala Val Leu Ser Glu Asp His Pro His Ala
Gly Gln Val Ser Val Gln Leu Pro Gly Thr Asn Tyr Val Gly Pro Gly Asn Gln Ala Gly Pro Gln
Ser Ala Val Asp Ser Ala Ala Arg Ile His Leu Leu Lys Asn Ile Lys Leu Gly Phe Gln Ala Gln Val Val
Thr His Trp Thr Val Ala Asp Ser Leu Gly Leu Ala Lys Thr Gly Gln Ser Leu Pro Glu Val Pro Ala
Lys Asp Tyr Phe Thr Leu Lys Ala Ala Pro Val Ala His Pro Gln Gly Ser Leu Pro Glu Val Pro Val
Tyr Asn Ala Ser Glu Lys Leu Tyr Pro Ser Met Thr Ser Val Asn Ser Ala Gly Arg Arg Ile Pro Gly Asn Ser Ser
```

FIG. 2-6

Met Thr Met Ile Thr Asn Ser Leu Ile Met Thr Ser Val Asn Ser Ala Glu Ala Ser Thr Gly Ala Gly Gly Gly
Gly Ser Asn Ser Val Lys Ser Met Trp Ser Glu Gly Ala Thr Phe Ser Ala Asn Ser Val Thr Cys Thr Phe Ser
Arg Gln Phe Leu Ile Pro Tyr Asp Pro Glu His His Tyr Lys Val Phe Ser Pro Ala Ala Ser Ser Cys His Asn
Ala Ser Gly Lys Glu Ala Lys Val Cys Thr Ile Ser Pro Ile Met Gly Tyr Ser Thr Pro Trp Arg Tyr Leu Asp Phe
Asn Ala Leu Asn Leu Phe Ser Pro Leu Glu Gln Phe Gln His Leu Ile Glu Asn Tyr Gly Ser Ile Ala Pro Asp
Ala Leu Thr Val Thr Ile Ser Glu Ile Ala Val Lys Asp Val Thr Asp Lys Thr Gly Gly Val Gln Val Thr
Asp Ser Thr Arg Gly Arg Leu Cys Met Leu Val Asp His Glu Leu Tyr Lys Tyr Pro Tyr Val Leu Gly Gln Gln
Asp Thr Leu Ala Pro Glu Leu Pro Ile Trp Phe Pro Val Tyr Phe Ala Tyr Leu Thr Val Gly Asp His Ser
Asn Thr Gln Gly Ile Ser Gly Leu Lys Ala Ser Met Ser Tyr Val Phe Tyr Val Pro Pro Glu Asn Leu
Ser Phe Gln Leu Leu Gly Thr Gly Met Tyr Asn Pro Leu Tyr Gly Ser Arg Leu Gly Val Pro Asp Thr Leu
Glu Gly Cys Ser Gln His Phe Tyr Glu Met Tyr Asn Pro Leu Tyr Gly Ser Arg Leu Gly Val Pro Asp Thr Leu
Gly Gly Asp Pro Lys Phe Arg Ser Leu Thr His Glu Gln Asn Ala Ile Gln Pro Gln Asn Phe Met Pro Gly Pro
Leu Val Asn Ser Val Ser Thr Leu Lys Glu Gly Asp Ser Asn Thr Gly Ala Gly Lys Ala Leu Thr Gly Leu Ser
Thr Gly Thr Ser Gln Asn Thr Arg Ile Ser Leu Arg Ile Ser Leu Arg Pro Val Ser Gln Pro Tyr His His Trp Asp Thr
Asp Lys Tyr Val Thr Thr Gly Ile Asn Ala Ile Ser Gly Gln Thr Thr Arg Gly Asn Ala Glu Asp Lys Glu Tyr
Gln Gln Gly Val Gly Arg Phe Pro Asn Gly Phe Glu Lys Gln Leu Leu Gln Leu Gly Leu Asn Met His Thr
Tyr Phe Pro Asn Lys Gly Thr Gln Gln Tyr Thr Asp Gln Ile Glu Arg Pro Leu Met Val Gly Ser Val Trp Asn
Arg Arg Ala Leu His Tyr Gly Ile Ser Gln Leu Trp Pro Asn Leu Asp Asp Ser Phe Lys Thr Gln Phe
Ala Ala Leu Gly Gly Trp Gly Leu His Gln Pro Pro Gln Ile Phe Leu Lys Gln Tyr Ala Val Gly Ile Met
Thr Val Thr Met Thr Phe Lys Leu Gly Pro Arg Lys Ala Thr Gly Arg Trp Asn Pro Gln Pro Gly Val Tyr Pro
Pro His Ala Ala Gly His Leu Leu Pro Tyr Val Leu Tyr Asp Pro Thr Ala Thr Asp Ala Lys Gln His His Arg His
Gly Tyr Glu Lys Pro Gly Leu Glu Leu Trp Thr Ala Lys Ser Arg Val His Pro Leu

FIG. 2-6A

| Thr | Met | Ile | Thr | Asn | Ser | Asp | His | Met |
|-----|-----|-----|-----|-----|-----|-----|-----|-----|
| Trp | Glu | Ser | Asp | Asp | Lys | Ser | Ala | Lys | Trp |
| Glu | Phe | Tyr | Glu | Lys | Val | Phe | Gly | Val | Phe |
| Leu | Lys | Asp | His | Tyr | Asn | Ile | Thr | Asp | Leu | Gln | Ile |
| Ser | Ser | Leu | Phe | Asp | Val | Ala | Arg | Leu | Asn | Glu | Asn | Lys | Asn |
| Ser | Pro | Asp | Leu | Tyr | Ser | His | Phe | Gln | Ile | Lys | Asn | Asn | Leu | Lys | Ser |
| Asp | His | Pro | His | Ala | Leu | Ser | Ser | Ser | Ser | His | Gly | Gln | Leu | Pro | Arg |
| Gly | Glu | Asn | Ala | Val | Leu | Ser | Glu | Asp | Leu | His | Ala | Glu | Pro | Gly | Gln |
| Val | Ser | Val | Gln | Leu | Pro | Gly | Thr | Asn | Tyr | Val | Gly | Pro | Gly | Asn | Glu |
| Leu | Gln | Ala | Gly | Pro | Pro | Gln | Ser | Ala | Val | Asp | Ser | Ala | Ala | Arg | Ile |
| His | Asp | Phe | Arg | Tyr | Ser | Gln | Leu | Ala | Lys | Gly | Ile | Ile | Asn | Pro | Tyr |
| Thr | His | Trp | Thr | Val | Ala | Asp | Glu | Gly | Leu | Leu | Lys | Asn | Ile | Lys | Asn |
| Glu | Thr | Gly | Phe | Gln | Ala | Gln | Val | Val | Lys | Lys | Asp | Tyr | Phe | Thr | Leu | Lys |
| Gly | Ala | Ala | Ala | Pro | Val | Ala | His | Phe | Gln | Asn | Gly | Ser | Leu | Pro | Glu | Val |
| Pro | Ala | Tyr | Asn | Ala | Ser | Glu | Lys | Tyr | Pro | Ser | Met | Thr | Ser | Asn | Ser | Val |
| Ser | Ala | Glu | Ala | Ala | Ser | Thr | Gly | Ala | Gly | Gly | Gly | Ser | Ala | Ser | Ser | Val | Thr |
| Lys | Ser | Met | Trp | Ser | Glu | Gly | Ala | Thr | Phe | Ser | Ala | Asn | Ser | Val | Thr |
| Cys | Thr | Phe | Ser | Arg | Gln | Phe | Leu | Ile | Pro | Tyr | Asp | Pro | Glu | His | His |
| Tyr | Lys | Val | Phe | Ser | Pro | Ala | Ala | Ser | Cys | His | Asn | Ala | Ser | Gly |
| Lys | Glu | Ala | Lys | Val | Cys | Thr | Ile | Ser | Pro | Ile | Met | Gly | Tyr | Ser | Thr |
| Pro | Trp | Arg | Tyr | Leu | Asp | Phe | Asn | Ala | Leu | Asn | Leu | Phe | Phe | Ser | Pro |
| Leu | Glu | Phe | Gln | His | Leu | Ile | Glu | Asn | Tyr | Gly | Ser | Ile | Ala | Pro | Asp |
| Ala | Leu | Thr | Val | Thr | Ile | Ser | Glu | Ile | Ala | Val | Lys | Asp | Val | Thr | Asp |
| Lys | Thr | Gly | Gly | Gly | Val | Gln | Thr | Thr | Asp | Ser | Thr | Thr | Gly | Arg | Leu |
| Cys | Met | Leu | Val | Asp | His | Glu | Tyr | Lys | Tyr | Pro | Val | Val | Leu | Gly | Gln |
| Gly | Gln | Asp | Thr | Leu | Ala | Pro | Glu | Leu | Pro | Ile | Trp | Tyr | Phe | Pro |
| Pro | Gln | Tyr | Ala | Tyr | Leu | Thr | Gly | Val | Asp | Val | Asn | Thr | Gln | Gly | Ile |
| Ser | Gly | Asp | Ser | Lys | Lys | Lys | Leu | Gly | Ser | Glu | Glu | Thr | Ser | Ala | Tyr | Val |
| Leu | Glu | His | Ser | Ser | Phe | Gln | Leu | Leu | Ala | Thr | Gly | Gly | Thr | Phe | Ala | Ser |
| Met | Ser | Tyr | Lys | Ser | Phe | Pro | Val | Pro | Val | Pro | Gly | Asn | Leu | Glu | Gly | Cys |
| Ser | Gln | His | Phe | Tyr | Glu | Met | Tyr | Asn | Pro | Leu | Tyr | Gly | Ser | Ser | Arg |
| Val | Asp | Leu | Gln |

FIG. 2-6B

```
Met Ser Lys Lys Ser Gly Lys Trp Trp Glu Ser Asp Asp Lys Phe Ala
 1           5                   10                  15
Lys Ala Val Tyr Gln Gln Phe Val Glu Phe Tyr Glu Lys Val Thr Asp
             20                  25                  30
Thr Asp Leu Glu Leu Ile Gln Ile Leu Lys Asp His Tyr Asn Ile Ser
                 35                  40                  45
Leu Asp His Pro Leu Glu Asn Pro Ser Ser Leu Phe Asp Leu Val Ala
         50                  55                  60
Arg Ile Lys Asn Asn Leu Lys Asn Ser Pro Asp Leu Tyr Ser His His
 65                  70                  75                  80
Phe Gln Ser His Gly Lys Leu Ser Asp His Pro His Ala Leu Ser Ser
                 85                  90                  95
Ser Ser Ser His Ala Glu Pro Arg Gly Glu Asn Ala Val Leu Ser Ser
             100                 105                 110
Glu Asp Leu His Lys Pro Gly Gln Val Ser Val Gln Leu Pro Gly Thr
             115                 120                 125
Asn Tyr Val Gly Pro Gly Asn Ile Leu Gln Ala Gly Pro Pro Gln Ser
         130                 135                 140
Ala Val Asp Ser Ala Ala Arg Ile His Asp Phe Arg Tyr Ser Gln Leu
145                 150                 155                 160
Ala Lys Leu Gly Ile Asn Pro Tyr Thr His Trp Thr Val Ala Asp Glu
                 165                 170                 175
Glu Leu Leu Lys Asn Ile Lys Asn Glu Thr Gly Phe Gln Ala Gln Val
             180                 185                 190
Val Lys Asp Tyr Phe Thr Leu Lys Gly Ala Ala Pro Val Ala His
         195                 200                 205
Phe Gln Gly Ser Leu Pro Glu Val Pro Ala Tyr Asn Ala Ser Glu Lys
     210                 215                 220
Tyr Pro Ser Met Thr Ser Val Asn Ser Ala Glu Ala Ser Thr Gly Ala
225                 230                 235                 240
Gly Gly Gly Gly Ser Asn Pro Val Lys Ser Met Trp Ser Glu Gly Ala
             245                 250                 255
Thr Phe Ser Ala Asn Ser Val Thr Cys Thr Phe Ser Arg Gln Phe Leu
             260                 265                 270
Ile Pro Tyr Asp Pro Glu His His Tyr Lys Val Phe Ser Pro Ala Ala
         275                 280                 285
Ser Ser Cys His Asn Ala Ser Gly Lys Glu Ala Lys Val Cys Thr Ile
290                 295                 300
Ser Pro Ile Met Gly Tyr Ser Thr Pro Trp Arg Tyr Leu Asp Phe Asn
305                 310                 315                 320
Ala Leu Asn Leu Phe Phe Ser Pro Leu Glu Phe Gln His Leu Ile Glu
             325                 330                 335
Asn Tyr Gly Ser Thr Ala Pro Asp Ala Leu Thr Val Thr Ile Ser Glu
             340                 345                 350
Ile Ala Val Lys Asp Val Thr Asp Lys Thr Gly Gly Val Gln Val
         355                 360                 365
Thr Asp Ser Ala Thr Gly Arg Leu Cys Met Leu Val Asp His Glu Tyr
370                 375                 380
Lys Tyr Pro Tyr Val Leu Gly Gln Gly Gln Asp Thr Leu Ala Pro Glu
385                 390                 395                 400
Leu Pro Ile Trp Val Tyr Phe Pro Pro Gln Tyr Ala Tyr Leu Thr Val
             405                 410                 415
Gly Asp Val Asn Thr Gln Gly Ile Ser Gly Asp Ser Lys Lys Leu Ala
             420                 425                 430
Ser Glu Glu Ser Ala Phe Tyr Val Leu Glu His Ser Ser Phe Gln Leu
     435                 440                 445
Leu Gly Thr Gly Gly Thr Ala Ser Met Ser Tyr Lys Phe Pro Pro Val
     450                 455                 460
Pro Pro Glu Asn Leu Glu Gly Cys Ser Gln His Phe Tyr Glu Met Tyr
465                 470                 475                 480
Asn Pro Leu Tyr Gly Ser
             485
```

FIG. 2-7

```
Met Thr Met Ile Thr Pro Ser Leu His Ala Cys Met Leu Val Asp His Glu Tyr Lys Tyr Pro Tyr Val Leu Gly
Gln Gly Gln Asp Thr Leu Ala Pro Glu Leu Pro Ile Trp Val Tyr Phe Pro Pro Gln Tyr Ala Tyr Leu Thr Val
Gly Asp Val Asn Thr Gln Gly Ile Ser Gly Asp Ser Lys Leu Ala Ser Glu Glu Ser Ala Phe Tyr Val Leu
Glu His Ser Ser Phe Gln Leu Leu Gly Thr Gly Thr Ala Ser Met Tyr Lys Phe Pro Val Pro Pro
Gln Asn Leu Glu Gly Cys Ser Ser Gln His Phe Tyr Glu Met Tyr Asn Pro Leu Tyr Gly Ser Arg Leu Gly Val Pro
Asp Thr Leu Gly Gly Asp Pro Lys Phe Arg Ser Leu Thr His Gly Ala Ile Gln Pro Gln Asn Phe Met
Pro Gly Pro Leu Val Asn Ser Val Ser Thr Lys Gly Leu Asp Ser Ser Asn Thr Gly Ala Lys Ala Leu Thr
Gly Leu Ser Thr Gly Thr Val Thr Ser Gln Asn Thr Arg Ile Ser Leu Arg Pro Gly Val Ser Gln Pro Tyr His His
Trp Asp Thr Asp Lys Tyr Val Thr Gly Ile Asn Ala Ile Ser His Gly Gln Thr Thr Tyr Gly Asn Ala Glu Asp
Lys Glu Tyr Gln Gln Gly Val Gly Arg Phe Pro Asn Glu Lys Gln Leu Lys Gln Leu Lys Lys Gln Leu Gly Leu Asn
Met His Thr Tyr Phe Pro Asn Lys Gly Thr Gln Gln Tyr Thr Asp Gln Ile Glu Arg Pro Leu Met Val Gly Ser
Val Trp Asn Arg Arg Ala Leu His Tyr Gly Ser Gln Leu Trp Ser Lys Ile Pro Asn Leu Asp Ser Phe Lys
Thr Gln Phe Ala Ala Leu Gly Gly Trp Gly Leu His Gln Pro Pro Gln Ile Phe Leu Lys Gln Tyr Ala Val
Gly Ile Met Thr Val Thr Met Thr Phe Lys Leu Gly Pro Arg Lys Ala Thr Gly Arg Trp Asn Pro Gln Pro Gly
Val Tyr Pro Pro His Ala Ala Gly His Leu Pro Tyr Val Leu Tyr Asp Thr Ala Thr Asp Lys Ala Lys Gln His
His Arg His Gly Tyr Glu Lys Pro Gly Glu Leu Trp Thr Ala Lys Ser Arg Val His Pro Leu
```

FIG. 2-7A

```
Met Thr Met Ile Thr Pro Ser Leu His Ala Cys Met Leu Val Asp His
Glu Tyr Lys Tyr Pro Tyr Val Leu Gly Gln Asp Thr Leu Ala
Pro Glu Leu Pro Ile Trp Val Tyr Phe Pro Gln Tyr Ala Tyr Leu
Thr Val Gly Asp Val Asn Thr Gln Gly Ile Ser Gly Asp Ser Lys Lys
Leu Ala Ser Glu Glu Ser Ala Phe Tyr Val Leu Glu His Ser Ser Phe
Gln Leu Leu Gly Thr Gly Gly Thr Ala Ser Met Ser Tyr Lys Phe Pro
Pro Val Pro Pro Glu Asn Leu Glu Gly Cys Ser Gln His Phe Tyr Glu
Met Tyr Asn Pro Leu Tyr Gly Ser Arg Leu Gly Val Pro Asp Thr Leu
Gly Gly Asp Pro Pro Lys Phe Arg Ser Leu Thr His Glu His Ala Ile
Gln Pro Gln Asn Phe Met Pro Gly Pro Leu Val Asn Ser Val Ser Thr
Lys Glu Gly Asp Ser Asn Thr Gly Ala Gly Lys Ala Leu Thr Gly
Leu Ser Thr Gly Thr Ser Gln Asn Thr Arg Ile Ser Leu Arg Pro Gly
Pro Val Ser Gln Pro Tyr His His Trp Asp Thr Asp Lys Tyr Val Thr
Gly Ile Asn Ala Ile Ser His Gly Gln Thr Thr Tyr Gly Asn Ala Glu
Asp Lys Glu Tyr Gln Gln Gly Val Arg Gly Phe Pro Asn Glu Lys Glu
Gln Leu Lys Gln Leu Gln Leu Asn Met His Thr Tyr Phe Pro Pro Asn
Lys Gly Thr Gln Gln Tyr Thr Asp Gln Ile Glu Arg Pro Leu Met Val
Gly Ser Val Trp Asn Arg Arg Ala Leu His Tyr Glu Ser Gln Leu Trp
Ser Lys Ile Pro Asn Leu Asp Asp Ser Phe Lys Thr Gln Ile Phe Ala Ala
Leu Gly Gly Trp Gly Leu Leu His Gln Pro Pro Gln Ile Phe Leu Lys
Ile Leu Pro Glu Ser Pro Ile Ala Val Gly Ile Gly Ile Lys Ser Met Gly Ile
Thr Thr Leu Val Gln Tyr Ala Val Gly Thr Gly Ile Met Thr Val Thr Met Thr
Phe Lys Leu Gly Pro Arg Lys Ala Thr Gly Ala Arg Trp Asn Pro Gln Pro
Gly Val Tyr Pro His Ala Ala Gly His Leu Pro Tyr Val Leu Tyr
Asp Pro Thr Ala Thr Asp Ala Lys Gln His His Arg His Gly Tyr Tyr
Lys Pro Glu Glu Leu Trp Pro Thr Ala Lys Ser Arg Val His Pro Leu Glu
```

FIG. 2-7B

```
Met Leu Val Asp His Glu Tyr Lys Tyr Pro Tyr Val Leu Gly Gln Gly
 1               5                   10                  15
Gln Asp Thr Leu Ala Pro Glu Leu Pro Ile Trp Val Tyr Phe Pro Pro
             20                  25                  30
Gln Tyr Ala Tyr Leu Thr Val Gly Asp Val Asn Thr Gln Gly Ile Ser
             35                  40                  45
Gly Asp Ser Lys Lys Leu Ala Ser Glu Glu Ser Ala Phe Tyr Val Leu
         50                  55                  60
Glu His Ser Ser Phe Gln Leu Leu Gly Thr Gly Gly Thr Ala Ser Met
 65                  70                  75                  80
Ser Tyr Lys Phe Pro Pro Val Pro Pro Glu Asn Leu Glu Gly Cys Ser
                 85                  90                  95
Gln His Phe Tyr Glu Met Tyr Asn Pro Leu Tyr Gly Ser Arg Leu Gly
             100                 105                 110
Val Pro Asp Thr Leu Gly Gly Asp Pro Lys Phe Arg Ser Leu Thr His
             115                 120                 125
Glu Asp His Ala Ile Gln Pro Gln Asn Phe Met Pro Gly Pro Leu Val
 130                 135                 140
Asn Ser Val Ser Thr Lys Glu Gly Asp Ser Ser Asn Thr Gly Ala Gly
145                 150                 155                 160
Lys Ala Leu Thr Gly Leu Ser Thr Gly Thr Ser Gln Asn Thr Arg Ile
             165                 170                 175
Ser Leu Arg Pro Gly Pro Val Ser Gln Pro Tyr His His Trp Asp Thr
             180                 185                 190
Asp Lys Tyr Val Thr Gly Ile Asn Ala Ile Ser His Gly Gln Thr Thr
             195                 200                 205
Tyr Gly Asn Ala Glu Asp Lys Glu Tyr Gln Gln Gly Val Gly Arg Phe
 210                 215                 220
Pro Asn Glu Lys Glu Gln Leu Lys Gln Leu Gln Gly Leu Asn Met His
225                 230                 235                 240
Thr Tyr Phe Pro Asn Lys Gly Thr Gln Gln Tyr Thr Asp Gln Ile Glu
             245                 250                 255
Arg Pro Leu Met Val Gly Ser Val Trp Asn Arg Arg Ala Leu His Tyr
             260                 265                 270
Glu Ser Gln Leu Trp Ser Lys Ile Pro Asn Leu Asp Asp Ser Phe Lys
             275                 280                 285
Thr Gln Phe Ala Ala Leu Gly Gly Trp Gly Leu His Gln Pro Pro Pro
             290                 295                 300
Gln Ile Phe Lys Tyr Tyr His Lys Val Gly Gln Leu Glu Val Leu Asn
305                 310                 315                 320
Gln Trp Glu Leu Leu Pro Phe Asn Met Pro Trp Glu Leu Gln Leu His
             325                 330                 335
Leu Asn Trp Gly Pro Val Lys Leu Gln Asp Gly Gly Ile Leu Asn Leu
             340                 345                 350
Glu Tyr Ile Pro Arg Thr Gln Gln Val Ile Tyr His Met Tyr Tyr Met
             355                 360                 365
Thr Pro Gln Leu Gln Met Gln Asn Asn Thr Thr Asp Met Asp Met Lys
             370                 375                 380
Ser Leu Lys Asn Cys Gly Gln Pro Lys Ala Val Cys Thr His
385                 390                 395
```

FIG. 2-8

Met Thr Met Ile Thr Pro Ser Leu Ala Ala Glu Ala Ser Thr Gly Ala Gly Gly Gly Ser Asn Ser Val Lys
Ser Met Trp Ser Glu Gly Ala Thr Phe Ser Ala Asn Ser Val Thr Cys Thr Phe Ser Arg Gln Phe Leu Pro
Tyr Asp Pro Glu His His Tyr Lys Val Phe Ser Pro Ala Ala Ser Ser Cys His Asn Ala Ser Gly Lys Glu Ala
Lys Val Cys Thr Ile Ser Pro Ile Met Gly Tyr Ser Trp Pro Thr Pro Arg Tyr Leu Asp Phe Asn Ala Leu Asn Leu
Phe Phe Ser Pro Leu Glu Phe Gln His Leu Ile Glu Asn Tyr Gly Ser Ile Ala Pro Asp Ala Leu Thr Val Thr
Ile Ser Glu Ile Ala Val Lys Asp Val Thr Asp Lys Tyr Gly Gly Val Gln Val Thr Asp Ser Thr Thr Gly
Arg Leu Cys Met Leu Val Asp His Glu Tyr Lys Tyr Pro Tyr Val Leu Gly Gln Gly Gln Asp Thr Leu Ala Pro
Glu Leu Pro Ile Trp Val Tyr Phe Pro Pro Gln Tyr Ala Tyr Leu Thr Val Gly Asp Val Asn Thr Gln Gly Ile
Ser Gly Asp Ser Lys Lys Leu Ala Ser Glu Glu Ser Ala Phe Tyr Val Leu Glu His Ser Ser Phe Gln Leu Leu
Gly Thr Gly Thr Ala Ser Met Ser Tyr Lys Phe Pro Pro Val Pro Glu Asn Leu Glu Gly Cys Arg Ser
Thr Asp Pro Arg Glu Phe Thr Gly Arg Arg Phe Thr Ser

FIG. 2-9

Met Thr Ile Thr Asn Ser Asp His Met Ser Lys Lys Trp Trp Glu Ser Asp Asp Lys Phe Ala Lys
Ala Val Tyr Gln Gln Phe Val Glu Phe Tyr Gly Lys Val Thr Gly Leu Glu Leu Ile Gln Ile Leu Lys
Asp His Tyr Asn Ile Ser Leu Asp Asn Pro Leu Ser Glu Leu Phe Asp Ser Leu Val Ala Arg Ile Lys
Asn Asn Leu Lys Ser Asn Ser Ser Asn Pro Asp Leu Tyr Ser His His Pro Ser Arg Ser Gln Leu Ser Glu Asp His Pro His
Ala Leu Ser Ser Ser Ser Ser His Ala Glu Val Ala Leu Pro Arg Gly Gln Asn Ala Val Leu Ser Glu Asp Leu Asp Ala Gly Leu His Lys
Pro Gly Gln Val Ser Val Asp Ser Ala Ala Arg Ile His Asp Phe Asn Tyr Val Gly Pro Gly Tyr Ser Gln Leu Gln Leu Ala Lys Gly Ile Asn Pro
Gln Ser Ala Val Ala Asp Ser Ala Ala Arg Ile His Asp Phe Asn Tyr Val Gly Pro Gly Tyr Ser Gln Leu Gln Leu Ala Lys Gly Ile Ala Gln Val
Tyr Thr His Trp Pro Thr Val Ala Asp Glu Leu Leu Lys Asn Glu Thr Gly Leu Tyr Phe Gln His Ala Gln Val
Val Lys Asp Tyr Phe Thr Leu Lys Gly Ala Ala Ala Pro Val Ala His Phe Gln His Gly Ser Leu Pro Glu Glu Val Pro
Ala Tyr Asn Ala Ser Glu Lys Tyr Pro Ser Met Thr Ser Val Asn Ser Ala Glu Ala Ser Thr Gly Ala Ala Gly Gly
Gly Gly Ser Asn Ser Val Lys Ser Met Trp Ser Glu Gly Ala Thr Phe Ser Ala Asn Ser Val Thr Cys Thr Phe
Ser Arg Gln Phe Leu Pro Tyr Asp Pro Glu His His Tyr Lys Val Phe Ser Pro Ala Ala Ser Ser Cys His
Asn Ala Ser Gly Lys Glu Ala Lys Val Cys Thr Ile Ser Pro Ile Met Gly Tyr Ser Thr Pro Trp Arg Tyr Leu Asp
Phe Asn Ala Leu Asn Leu Phe Phe Ser Pro Leu Glu Phe Gln His Leu Ile Glu Asn Tyr Gly Ser Ile Ala Pro
Asp Ala Leu Thr Val Thr Ile Ser Glu Ile Ala Val Lys Asp Val Thr Asp Lys Tyr Gly Gly Val Gln Val
Thr Asp Ser Thr Thr Gly Arg Leu Cys Met Leu Val Asp His Glu Tyr Lys Tyr Pro Gln Tyr Ala Phe Tyr Val Leu Thr Val
Gln Asp Pro Leu Ala Pro Glu Leu Pro Ile Trp Val Tyr Phe Pro Pro Gln Tyr Ala Tyr Leu Thr Val Gly Asp
Val Asn Thr Gln Gly Val Ser Gly Asp Ser Lys Lys Leu Ala Ser Glu Glu Ser Met Ser Tyr Lys Phe Pro Pro Val Leu Glu His
Ser Ser Phe Gln Leu Leu Gly Thr Gly Thr Ala Ser Met Ser Tyr Lys Phe Pro Pro Val Pro Glu Asn
Leu Glu Gly Cys Ser Gln His Phe Tyr Glu Phe Thr Gly Arg Arg Phe Thr Ser Ser Arg Val Asp Leu Gln

FIG. 2-10

```
Met Thr Ile Thr Asn Ser Asp His Met Ser Lys Lys Ser Gly Lys Trp Trp Glu Ser Asp Asp Lys Phe Ala Lys
Ala Val Tyr Gln Gln Phe Val Glu Phe Tyr Glu Lys Val Thr Gly Thr Asp Leu Gly Leu Ile Gln Ile Leu Lys
Asp His Tyr Asn Ile Ser Leu Asp Asn Pro Leu Asn Pro Ser Ser Leu Phe Asp Leu Val Ala Arg Ile Lys
Asn Asn Leu Lys Asn Ser Pro Asp Leu Tyr Ser His His Gly Gln Ser Glu Ser Asp His Pro His
Ala Leu Ser Ser Ser His Ala Glu Pro Arg Gly Glu Asn Ala Val Leu Ser Ser Gln Leu Asp Leu His Lys
Pro Gly Gln Val Ser Val Gln Leu Pro Gly Thr Asn Tyr Val Gly Pro Gly Asn Glu Leu Gln Ala Gly Pro Pro
Gln Ser Ala Val Asp Ser Ala Ala Arg Ile His Asp Phe Arg Tyr Ser Gln Leu Ala Lys Leu Gly Ile Asn Pro
Tyr Thr His Trp Thr Val Ala Asp Glu Glu Leu Lys Asn Ile Lys Asn Glu His Gly Phe Gln Ala Gln Val
Val Lys Asp Tyr Phe Thr Leu Lys Gly Ala Ala Pro Val Ala His Phe Gln Gln Gly Ser Leu Pro Glu Val Pro
Ala Tyr Asn Ala Ser Glu Lys Tyr Pro Ser Met Thr Ser Val Asn Ser Ala Glu Ala Ser Thr Gly Ala Gly Gly
Gly Gly Ser Asn Ala Val Lys Ser Met Trp Ser Glu Gly Ala Thr Phe Ser Ala Asn Ser Val Thr Cys Thr Phe
Ser Arg Gln Phe Leu Ile Pro Tyr Asp Pro Glu His His Tyr Lys Val Phe Ser Pro Ala Ala Ser Ser Cys His
Asn Ala Ser Gly Lys Glu Ala Lys Val Cys Thr Ile Ser Pro Ile Met Gly Tyr Ser Thr Pro Trp Arg Tyr Leu Asp
Phe Asn Ala Leu Asn Leu Phe Ser Pro Leu Glu Phe Gln His His Leu Ile Glu Asn Tyr Gly Ser Ile Ala Pro
Asp Ala Leu Thr Val Thr Ile Ser Glu Ile Ala Val Lys Asp Val Thr Asp Lys Thr Gly Gly Gly Val Gln Val
Thr Asp Ser Thr Gly Arg Leu Cys Ser Asn
```

IMMUNOLOGICALLY ACTIVE PEPTIDES OR POLYPEPTIDES FROM THE PARVOVIRUS B19

This application is a continuation of application Ser. No. 08/214,658, filed Mar. 16, 1994, now abandoned, which is a continuation in part of application Ser. No. 07/917,096, filed Aug. 4, 1992, now abandoned which is a 371 of PCT/DE91/00106, filed Feb. 8, 1991

The human parvovirus B19 (for short hereinafter: B19) was discovered by chance in 1975 in plasma samples from blood donors (Cossart, Y. E., Field, A. M., Cant, B., Widdows, D.: Parvovirus-like particles in human sera. Lancet I (1975) 72–73) by countercurrent electrophoresis. In recent years it has been shown that B19 may cause an aplastic crisis in patients with chronic haemolytic crisis (sic), and is the aetiological agent of erythema infectiosum (EI).

Under the electron microscope, B19 has a size of about 20 nm. The particles have an icosahedric symmetry. Besides the virus particles there are also seen to be "empty" capsids which contain no DNA. The density in $CsCl_2$ (sic) is 1.36–1.40 g/ml. The virus genome consists of a single-stranded DNA of 5.4 kb. The nucleotide sequence of the genome of a B19 parvovirus has been derived from a clone which contained virtually the complete viral genome (R. O. Shade et al. Journal of Virology (1986) p. 921). In each case only one DNA strand, either of the plus or the minus orientation, is packaged into each virus particle. B19 is an autonomous parovirus (sic), that is to say requires no helper virus for replication.

The capsid consists of two polypeptides with molecular weights of 83 kDa (VP1) and 58 kDa (VP2). In addition, three non-structural proteins of 52, 63 and 71 kDa can be detected.

The DNA codes in the 5' region for the structural proteins of the capsid. The coding regions of the structural proteins are identical apart from an additional N terminus of VP1. This difference is caused by splicing processes at the mRNA level, in which in the case of VP2 the translational start for VP1 is taken out and thus translation can start only with the shorter VP2.

Investigations on various B19 isolates found world-wide have shown that these differ in part at the DNA level by the restriction enzyme pattern. These differences do not, however, correlate with the clinical spectrum of B19 infection.

It has not been possible to date to find a permanent cell line in which B19 can be grown. There has been just as little success to date in establishing an experimental animal model for B19. B19 can, however, be grown in primary bone marrow cells in the presence of erythropoietin. It has thus been possible to clarify the mechanism of replication of the virus and show that cells of erythropoiesis are the target cells of this infection. Inoculation of B19 cells in fetal erythropoietic cells and erythroblasts of a patient with chronic myeloid leukaemia has now succeeded.

B19 causes erythema infectiosum (infectious erythema) which is an infectious disease which usually has a benign course and mostly occurs between the ages of childhood and early adulthood. B19 infection may in addition cause aplastic crises in patients with chronic haemolytic anaemia (sickle cell anaemia etc.) and chronic bone marrow aplasias in patients with inborn or acquired immunodefficiency states.

In pregnancy B19 infection may in about 10–15% result in hydrops fetalis with resulting interuterinal (sic) death. Furthermore, B19 is associated with the occurrence of Schonlein-Henoch purpura.

As a rule, B19 is transmitted by droplet infection but also by antigen-positive conserved blood and coagulation products.

Since no permanent cell line in which B19 can be obtained in large amounts is yet known, there is thus a lack of a source for obtaining antigen for diagnostic tests. To date one has made do with B19 virus discovered by chance in conserved blood from donors who are just in the viraemic stage of infection.

The object of the present invention is to provide immunologically active polypeptides which permit, with the test systems presented here, detection of B19-specific antibodies of the IgG and IgM class. This results in the following possible applications:

Serodiagnosis of acute or previous B19 infections in dermatology, haematology, gynaecology, rheumatology and paediatrics.

Determination of the B19 immune status in pregnant women.

Investigation of conserved blood or donated plasma to exclude transmission of B19 antigen, since it is highly probable that transmission of 1319 virus is no longer possible by anti-B19 IgG positive blood or plasma.

Selection of anti-B19 positive plasma donors for production of B19 hyperimmunoglobulin products.

There is a pressing need for the introduction of test reagents because of the broad clinical spectrum of the diseases caused by B19, and of the risk to B19-seronegative pregnant women.

It has emerged that utilisable immunologically active polypeptides cannot be prepared directly. Preparation of short peptides by genetic engineering is, just like that of large polypeptides, possible in a satisfactory yield only when suitable expression vectors are used. Although relatively short peptides can be easily prepared by synthesis, more accurate knowledge of the immunological activity is necessary.

The invention relates to immunologically active peptides which have a part of the amino-acid sequence of the capsid proteins VP 1 or VP 2 of parvovirus B19. These peptides are characterised in that they are free of impurities which interfere with the detection of antibodies directed against parvovirus B19. This property is of great importance since it is not possible to utilise those peptide preparations which contain, by reason of the preparation, components which react with the antibodies to be detected. One example of an unwanted impurity of this type is protein A, which is able to react specifically with the Fc portion of IgG antibodies. A particular advantage of the immunologically active peptides according to the invention is that they can be prepared in good yield by the preparation process according to the invention. This is because, if the antigens required for a diagnostic test are not synthesised in an adequate amount in the preparation process, it is not possible to obtain the required yield after the subsequent purification processes.

It has furthermore been possible within the scope of the present invention to determine short peptide segments from VP 1, more accurately from the region of VP 1 which does not coincide with VP 2, whose epitopes are suitable for reliable detection of antibodies against parvovirus B19 in the investigation fluids, especially sera. This region is called VP 1–VP 2 hereinafter. FIG. 3 shows by way of example the arrangement of some peptides (PAPEP 1–PAPEP 8) in the region (VP 1–VP 2). Although these peptides are preferred, it is equally possible to employ other peptides with 8–50 amino acids, preferably 10 to 32 amino acids, from the VP 1–VP 2 region. This region approximately corresponds to the polypeptide PAN1 which is depicted in FIG. 2-1.

In a preferred embodiment of the present invention, this small, immunodominant and B19-specific region is employed in the serological test. It is particularly preferable in this connection to employ a mixture of synthetic peptides, these peptides having the amino-acid sequences PAPEP 1–PAPEP 8 shown in Example 3.

In another preferred embodiment of the present invention, the amino-acid sequences which are depicted in FIG. 2 of the immunologically active peptides PAN-1, PAN-2, PAN-3, PAN-4, PCE, PANSE AND (sic) PAPST prepared by genetic engineering are employed. It is as a rule sufficient in this case to use one peptide in the test. It is possible, however, in special cases also to employ two or more of these peptides.

The peptides according to the invention can be prepared either by synthesis or by genetic engineering. The short peptides, which are explained in detail in Example 3, are preferably prepared by synthesis. The longer peptides are, however, preferably prepared by genetic engineering.

Firstly, the coding regions of the viral DNA were amplified from the serum of an infected patient by means of two polymerase chain reactions (PCR) and cloned in plasmids for further growth in *Escherichia* (*E.*) *coli*. After further subcloning steps, various regions therefrom were then expressed by genetic engineering in *E. coli*, and the antigens resulting therefrom were investigated for their use for detecting antibodies against the virus. Direct preparation of the peptides according to the invention in expression vectors is impossible because of various difficulties. For this reason, according to the invention, the viral protein segment is fused to a protein amenable to stable expression. This fusion protein can be employed directly after purification as antigen for IgG detection. However, the parvovirus-specific portion is preferably cleaved off by suitable methods, further purified and then employed for serological tests.

The present invention furthermore relates to test kits for the determination of antibodies which are directed against parvovirus B19. The immunologically active peptides according to the invention can in principle be used in all diagnostic test kits for detecting antibodies against parvovirus B19. In a preferred embodiment of the test kits according to the invention, the solid phase of suitable microtitre plates or polystyrene beads is coated with the immunologically active peptides according to the invention. After incubation with the investigation fluid (serum sample) in a suitable dilution, and after customary washing steps, enzyme- or radioactively labelled anti-human IgG is added. The extent of substrate conversion or of the bound radioactivity then shows whether antibodies directed against parvovirus B19 are present in the serum sample.

The test kits according to the invention are normally supplied to laboratories of physicians, hospitals, investigation facilities etc. They usually contain all the reagents required for carrying out the test. Customary test reagents such as buffer solutions etc. are, however, sometimes not included. As a rule, the test kits contain microtitre plates or polystyrene beads which are coated either with one or more peptides according to the invention or with anti-antibodies. The test kits may furthermore contain, depending on the test principle, one or more peptides according to the invention. Finally, the test kits also embrace an indicator component which makes it possible to quantify the test result.

In other preferred test kits, the antigens are bound to the solid phase of microtitre plates or polystyrene beads. After incubation of the test serum, and suitable washing and saturation steps, a specific enzymatically or radioactively labelled antibody against the B19 antigens is added and its substrate conversion or the bound radioactivity is measured. Since this takes the form of an inhibition test, a small substrate conversion or low radioactivity indicates the presence of specific antibodies.

It is likewise possible to employ peptides according to the invention coupled to solid phases for detecting IgM antibodies against B19. In this detection method, firstly the IgG antibodies are eliminated by adding beads coated with protein A to the investigation fluids. Bound antibodies are then detected using an anti-human IgM antibody which is enzymatically or radioactively labelled.

The principle of the so-called $\mu$-capture assay is used in another preferred test kits First the IgM from the investigation fluid (serum) is bound by means of anti-human IgM antibodies bound to the solid phase. The immunologically active peptides according to the invention are then added. The extent of the binding of the antigens and thus the amount of anti-B19 IgM present can be effected by either the antigens being radioactively labelled or labelled with other substances (digoxigenin, avidin) and thus being detectable, or by employing a second labelled antibody against the B19 antigens and measuring its binding.

Very particularly preferred within the scope of the present invention are ELISA (enzyme linked immunosorbent assay) test kits.

Also provided according to the invention are DNA sequences which can be used for direct detection of the virus in investigation samples (sera, biopsies, etc.). Two DNA primers which attach themselves specifically to DNA regions in VP 1 are preferably used. It is then possible by means of a commercially available polymerase chain reaction kit to achieve amplification of the region lying between them. Amplified DNA which has then been immobilised in a suitable way is detected by a suitable DNA sequence. This DNA employed for the hybridisation is prepared with the aid of a plasmid which contains the DNA region lying between the two primers.

It is self-evident that the primer sequences must not be present in the DNA employed for the hybridisation. The sequence of the primers used, and the arrangement with respect to one another, is depicted in FIG. 1.

Finally, vaccines against parvovirus B19 are also made available within the scope of the present invention. This entails the immunologically active peptides according to the invention being administered, optionally several times, together with suitable adjuvants to the people to be protected. The production of antibodies elicited by this can effect protection from infection with parvovirus B19.

EXAMPLE 1

Obtaining Parvovirus B19 VP 1-and VP 2-encoding Sequences from Patient's Serum

Viral DNA was isolated from 1 ml of serum from a patient with acute infection (erythema infectiosum) by proteinase K digestion in 1% SDS, phenol extraction and subsequent alcohol precipitation (this and all the following steps for obtaining, processing and expressing DNA, as well as the preparation of recombinant proteins and fundamental steps for the purification thereof, are described in detail in: Maniatis, T., Fritsch, E. F., Sambrook, J. (1982) Molecular cloning. Cold Spring Harbor, N.Y.). This DNA was taken up in 50 $\mu$l of TE buffer and then 1 $\mu$l samples were employed for the amplification by means of the polymerase chain reaction and synthetic oligodeoxynucleotides. Two pairs of primers were used for the amplification of the coding regions of the surface proteins; one of these for obtaining the VP 1 portion, and the second pair for the complete VP p oligodeoxynucleotides used as primers have at each of their, 5' ends sequences which are not homologous with the parvovirus sequence, code for restriction enzyme cleavage sites and are therefore suitable for cloning the DNA fragments resulting from the PCR into suitable vectors. The primers identified by O-1 to O-5 in FIG. 1 were used.

In each case five mixtures each containing 1 $\mu$l of isolated parvovirus DNA were amplified with the two pairs of primers in a volume of 100 $\mu$l. The conditions for this were: 1.5 min denaturation at 94° C., 2 min attachment of the primers at 45° C., 4 min synthesis at 72° C.; total of 50 cycles; buffer, substrates and Taq polymerase were employed for this as stated by the manufacturer (Cetus/Perkin-Elmer, Überlingen, FRG).

The amplified DNA fragments from the two different mixtures (for VP 1 and VP 2) were in each case combined, precipitated by alcohol precipitation, washed with 70% alcohol, dried, dissolved in a volume of 200 $\mu$l of TE buffer and digested with the restriction enzymes EcoRI and HindIII. Fractionation of the fragments by electrophoresis in a 1.2% agarose gel was then followed by isolation of the corresponding DNA bands (709 bp for VP 1, 1704 bp for VP 2) and insertion into the EcoRI and HindIII sites of the vector PUC12 (Pharmacia, Sweden). After transformation of the plasmids into *E. coli* JM109 (Pharmacia, Sweden), bacterial clones with parvovirus DNA inserts were characterised by restriction digestion. The corresponding zones were given the names pUC12PAN for the region encoding the VP 1 portion and pUC12VP2 for the VP 2-encoding region.

EXAMPLE 2

Preparation by Genetic Engineering of VP 1 Portion and VP 2 from *E. coli* Cells a) VP1 portion:

1) PAN-1

The VP1-encoding region was isolated from the plasmid pUC12PAN with BclI and HindIII (see FIG. 1, the HindIII site originates from the pUC vector) and inserted behind the 3' end of a truncated β-galactosidase gene of the vector (for example pBD2) into the BamHI and HindIII restriction cleavage sites. *E. coli* cells with plasmids resulting therefrom express after induction with IPTG a β-gal::VP1 fusion protein (about 67 kDA) in large quantity, which reacts very strongly with anti-parvovirus B19-positive sera in an immunoblot (Western blot). Purification of this protein can be achieved very easily with conventional methods utilising the insolubility of the protein. After lysis of the cells, the pellet fraction is washed with detergents such as Triton-X100 and octyl gluco-pyranoside, and the fusion protein is subsequently dissolved with 8M urea/1% mercaptoethanol and separated from cellular impurities by DEAE chromatography with an NaCl gradient.

The VP1 portion can be cleaved off the fusion protein by BrCN cleavage since the VP1 protein sequence starts with a methionine, and this amino acid no longer appears in the fragment itself; by contrast, methionine occurs relatively often in the bacterial fusion portion so that this portion is broken up into very small fragments. After cleavage in 35% formic acid and 0.1 mg/ml BrCN at room temperature for 4 h, the sample was lyophilised, dissolved in 8M urea, 2 mM DTE (sic) (dithiothreitol) and purified by DEAE chromatography in an NaCl gradient. The VP1 fragment resulting therefrom was called PAN-1 and can be used directly for serological determinations. The amino-acid sequence is indicated in FIG. 2-1.

Further constructs generated were plasmids which code for fusion proteins consisting of the glutathione S-transferase from Schistosoma japonicum (Smith, D. B. and Johnson, K. S.: Single step purification of polypeptides expressed in Escherichia coli as fusions with glutathione S-transferase. Gene, 67 (1988) 31–40) and the VP1 portion. However, it is also possible to use another fusion partner as long as it does not interfere with the diagnostic test.

2) PCE:

The B19 DNA fragment was isolated from pUC12PAN after BclI/PvuII digestion (618 bp) and integrated into the BamHI and SmaI sites in pGEX1 (pGEX1PAN). The resulting 52 kDA fusion protein was purified from the supernatant by means of glutathione-coupled agarose and employed as antigen for the serological tests in Example 4 (name:PCE). The amino-acid sequence of this antigen is shown in FIG. 2-2.

3) PAN-2:

A 458 bp fragment was isolated from pUC12PAN with BclI/HincII and, after intermediate clonings in other vectors, inserted into pGEX2 (pGEX2PAN). Insertion of the fragment in the same reading frame can also be achieved by using oligodeoxynucleotides. At the fusion site of glutathione S-transferase and the VP1 segment is the amino-acid sequence which is recognised by thrombin, so that the B19 portion can be cleaved off the fusion partner by this enzyme. It is also possible to use any other fusion partner as long as it has this protease recognition sequence. The amino-acid sequence of the antigen, as well as fused-on foreign amino acids (in bold print) is indicated in FIG. 2-3.

4) PAN-3:

A 458 bp fragment was isolated from pUC12PAN with BclI/HincII and, after intermediate clonings in other vectors, inserted into pGEX3 (pGEX3PAN). Insertion of the fragment in the same reading frame can also be achieved by using synthetic oliaodeoxynucleotides. At the fusion site of glutathione S-transferase and the VP1 segment is the amino-acid sequence which is recognised by the protease factor Xa, so that the B19 portion can be cleaved off the fusion partner by this enzyme. It is also possible to use any other fusion partner as long as it has this protease recognition sequence. The amino-acid sequence of the antigen, as well as fused-on foreign amino acids (in bold print) is indicated in FIG. 2-4.

5) PAN-4:

The complete B19 DNA insert was obtained from pUC12PAN by BclI and PstI digestion and, after various intermediate cloning steps, inserted into the vector pGEX2. This resulted in the plasmid pGEX2PAN. Insertion of the fragment in the same reading frame can also be achieved by using synthetic oligodeoxynucleotides. At the fusion site of glutathione S-transferase and the VP1 segment is the amino-acid sequence for the protease thrombin, so that the B19 portion can be cleaved off the fusion partner by this enzyme. It is also possible to use another suitable fusion partner if it has this protease recognition sequence. The amino-acid sequence of the antigen, as well as fused-on foreign amino acids (in bold print) is indicated in FIG. 2-5.

Purification of the antigens can be achieved by simple affinity chromatography with a glutathione-coupled gel matrix.

For further purification of the fusion proteins based on pGEX2 and 3, the B19 portion was cleaved off by digestion with trombin (sic) or factor X as stated by the manufacturer (Boehringer Mannheim). The fragments were then purified again by affinity chromatography. The S-glutathione (sic) transferase can in this case be selectively fished out, the parvovirus protein portion is to be found in the flow-through and can be employed after a final DEAE chromatographic fractionation in serological tests.

However, as an alternative to this, the protease can also be added directly to the glutathione-coupled gel suspension with the fusion protein bound on. After an incubation time of about 1 h, the VPI (sic) fragment which has been cleaved off can be washed out of the gel, while the glutathione S-transferase portion remains bound to the gel matrix.

b) VP-2 portion:

1) VP-2

Owing to the choice of the PCR primers and of the vector, the coding region for VP2 is already in the correct reading frame in the plasmid pUC12VP2 and can be purified after induction with IPTG from the insoluble fraction of the bacterial lysate, in a similar way to that described for pBD2PAN. The amino-acid sequence of the recombinant antigen is shown in FIG. 2-6.

2) PANSE:

It emerged, surprisingly, that a truncation of the VP2-encoding sequence is associated with a considerable increase in the protein yield, that this truncated antigen can be stably expressed, is not degraded even during purification, and still has the same reactivity with anti-B19 positive sera too. This expression plasmid (pUC19PANSE) was obtained by truncating the 5' region of VP2 by 355 bp as far as an NsiI site. This fragment was inserted into pCU19 (Pharmacia, Sweden) which has the same reading frame in the lacZ peptide as the B19 sequence. Since, because of the PCR primers, a HindIII site is located at the 3' end, it was necessary also to produce an EcoRI site by intermediate cloning in order to be able to insert the required fragment into the PstI and EcoRI sites of pUC19.

The antigen with a size of about 38 kDa (PANSE) can be separated from impurities very simply from the pellet fraction of the bacterial lysate after dissolving in 4M urea by DEAE chromatography. The amino-acid sequence of the antigen is indicated in FIG. 2-7.

3) PAPST:

A fragment 716 bp in size which encodes the N-terminal region of VP-2 was isolated from the plasmid pUC12VP2 by PstI digestion. After insertion of the fragment into the vector pUC9 (Pharmacia, Sweden) in the same orientation of the reading frames as the lacZ of the vector (characterised by restriction enzyme digestion), the B19 antigen with a size of about 33 kDa is produced in very large quantity (about 10% of the total E. coli protein). Purification can take place in a similar way as for pBDAN from the insoluble constituents by dissolving in 8M urea and subsequent DEAE chromatography. The amino-acid sequence is depicted in FIG. 2-8.

c) Complete VP1/VP2:

The plasmid pUC12PAN was opened with PstI and HindIII, and the VP2 encoding region from pUC12VP2 was inserted after HindIII and Partial PstI digestion as 1.7 kb fragment (pUC12VP1/2).

Expression of VP1/2-containing antigens in E. coli:

1) PAV-1-B:

pUC12VP1/2 was cut with EcoRI and BamHI, and a DNA band 1466 bp in size was isolated and subsequently inserted into the EcoRI/BamHI sites of the vector pUC18stop. pUC18 stop resembles the abovementioned pUC vectors; however, it differs from the latter by containing between the PstI and HindIII site a synthetic oligodeoxynucleotide which codes for translation stop signals and for the stop of transcription. The polylinker region of the vector identified in applicants' sequence listing as sequence as sequence no. 23; thus has the following sequence:

```
ATG ACC ATG ATT ACG ATT TCG AGC
TCG GTA CCC GGG GAT CCT
CTA GAG TCG ACC TGC AGT AAT TAA
TTA GAT CTC GAG CCC GCC
TAA TGA GCG GGC TTT TTT AAG CTT
```

(The restriction cleavage sites EcoRI-GAATTC, BamHI-GGATCC, PstI-CTGCAG, BglII (sic)-AGATCT and HindIII-AACGTT (sic) are indicated by bold print)

The vector (pUC-V1-B) obtained in this way encodes the VP-1 structural protein from the start up to amino acid 486 followed by some amino acids of the pUC polylinker and is terminated by the stop codon of the inserted oligodeoxynucleotide. The expressed antigen (PAV-1-B) is produced in very good yield after IPTG induction in the *E. coli* cells and has a size of 60 kDa. Its amino-acid sequence is depicted in FIG. 2-9, amino acids emphasised by bold print are not B19-specific and are encoded by pUC sequences. The reactivity with anit-B19-positive (sic) sera is very good and efficient purification can be achieved by removing soluble *E. coli* proteins, dissolving in 8M urea and conventional ion exchange chromatography (as described).

2) PAV-1-N:

The vector pUCVP-1-B described above was digested with EcoRI and NsiI. The band 1137 bp in size produced in this way was inserted into the vector pUCl8stop into the EcoRI and PstI sites (see above). The resulting vector pUCVP-1-N encodes the structural protein from the start up to amino acid 377; the antigen (PAV-1-N) is produced after IPTG induction in the *E. coli* cells somewhat less well than the antigen PAV-1-B described above. It is 45 kDa in size, and the reactivity with anti-B19 sera is good. The amino-acid sequence is indicated in FIG. 2-10, amino acids with bold print are encoded by the pUC vector and are not B19 specific. Purification of the antigen can be achieved as for PAV-1-B.

3) Expression of the antigens described under c)1) and c)2) as GST fusion proteins The two vectors pUCVP-1-B and pUCVP-1-N were digested with EcoRI/BglII and the resulting bands about 1480 bp and 1150 bp, respectively, in size were isolated, with the translation stop signals introduced together with the pUC18stop being transferred too. (The BglII site is indicated in the pUC18stop polylinker sequence indicated above, and the BclI site (TGATCA) immediately before the start of translation was introduced with the primers used for the DNA amplification—see FIG. 1, 0-1). The two fragments which encode the same 5' sequences but regions of different length of VP-1 were then inserted into the vector pGEX-1 described above. Since pGEX-1 has only the SmaI and EcoRI restriction cleavage sites available for insertion of the 3' end of a fragment, it was initially necessary also to produce a site compatible for SmaI (blunt end). This was effected by inserting the two DNA fragments into the EcoRI and BamHI (compatible with BglII) restriction sites of the vector pIC20H (The pIC plasmid and phage vectors with versatile cloning sites for recombinant selection by insertional inactivation, J. L. Marsh, M. Erfle and E. J. Wykes, Gene, 32 (1984) 481–485). The two fragments were then isolated in turn from the two resulting vectors with BclI and HincII (blunt end cleavage) and inserted into pGEX-1 in BamHI and SmaI. Since HincII also cuts in the B19 sequence, the two fragments were isolated by a partial HincII digestion.

The two pGEX vectors now express fusion proteins consisting of the glutathione S-transferase followed by the two VP-1 segments of different length. The fragment originating from pUCVP-1-B and now located in pGEXVP-1-B yields a fusion protein of about 87 kDa; the smaller fragment encoding only up to amino acid 377 a fusion protein 72 kDa in size. The amino-acid sequences are indicated in FIG. 2-9 and 2-10. The only difference is that the five N-terminal amino acids are omitted and instead replaced by glutathione S-transferase.

4) Further expression of VP1/VP2:

A 2.4 kb fragment was isolated after EcoRI and HindIII digestion from the plasmid pUC12VP1/2 with the complete VP1 and VP2 encoding region and inserted into the eukaryotic expression vector pMDIII (Motz, M., Deby G., Jilg, W., Wolf, H.: Expression of the Epstein-barr (sic) virus major membrane proteins in Chinese hamster ovary cells. Gene, 44 (1986) 353–359. (Obtainable from ATCC)) after EcoRI and HindIII digestion. This plasmid was subsequently linearised again with a SalI, and a 2.4 kb SalI fragment with a dihydrofolate reductase gene (DHFR) and regulatory sequences was also inserted. The plasmid pMDIIIVP1/2 obtained in this way was transfected into DHFR-negative CHO cells. Colonies resulting after selection on alpha-minus medium (gibco (sic)) were isolated and amplified after washing out with increasing concentrations of methotrexate (MTX). Particles with VP1/VP2 can be purified from the culture supernatant from these cell cultures.

Furthermore, the 2.4 kb fragment from pUC12VP1/2 was inserted after EcoRI/HindIII digestion into a vector which has, besides the HindIII site, also a BamHI site. The parvovirus portion from this intermediate construct was then isolated as BclI and BamHI fragment and inserted into the BamHI site of a baculovirus expression vector (various constructs can be used). (The BclI site is located immediately in front of the translational start of VP1, it is encoded by the PCR primers, see FIG. 1; the BamHI digestion must be carried out partially since there is also a site of this type still present in the parvovirus sequence.). After co-transfection of the resulting plasmid with wild-type baculovirus DNA into an insect cell culture line, cells which have no so-called inclusion bodies were isolated. The VP1 which is produced intracellularly can be purified in large quantity from those cells in which the baculovirus polyhedrin gene is replaced by the VP1/2 gene.

5) Expression of VP-2:

Furthermore, expression of the smaller B19-VP-2 was obtained using recombinant baculoviruses. For this, the VP-2-encoding plasmid pUC12VP (see Example 1) was digested with EcoRI and HindIII, and the resulting 1.7 kb fragment was inserted into an abovementioned vector which has, besides the HindIII site, also a BamHI site. The parvovirus portion was then isolated as BclI (sic) and BamHI fragment from this intermediate construct and inserted into the BamHI site of a baculovirus expression vector (various constructs can be used). (The BclI (sic) site is located immediately in front of the translational start of BP2, it is encoded by the PCR primers, see FIG. 1, O-3; the BamHI digestion must be carried out partially since there is also a site of this type still present in the parvovirus sequence). After co-transfection of the resulting plasmid with wild-type baculovirus DNA into an insect cell culture line, cells which have no so-called inclusion bodies were isolated. VP2 can be purified in large quantity as particles from those cells in which the baculovirus polyhedrin gene is replaced by the VP2 gene. These particles are particularly suitable for use in the $\mu$-capture test.

EXAMPLE 3

Synthetic Peptides with Immunodominant Epitopes

The reaction patterns of the bacterial expression products (especially pGEX::VP1 fusion constructs) with parvovirus-positive sera in a Western blot lead to the surprising conclusion that a short fragment from the VP1 portion suffices to identify all IgG-positive parvo sera.

The fragment can be covered with the following peptides which can be produced by synthesis:

```
PAPEP-1 identified in applicants' sequence
listing as sequence no. 2:
Ser Lys Lys Ser Gly Lys Trp Trp Glu Ser
Asp Asp Lys Phe Ala Lys Ala Val Tyr PAPEP-2 identified in applicants' sequence
listing as sequence no. 3:
Leu Lys Asp His Tyr Asn Ile Ser Leu Asp
Asn Pro Leu Glu Asn Pro Ser Ser PAPEP-3 identified in applicants' sequence
listing as sequence no. 4:
Ile Lys Asn Asn Leu Lys Asn Ser Pro Asp
Leu Tyr Ser His His Phe Gln Ser His Gly
Gln Leu Ser Asp His Pro His Ala PAPEP-4 identified in applicants' sequence
listing as sequence no. 5:
Ser Ser His Ala Giu Pro Arg Gly Glu Asn
Ala Val Leu Ser Ser Glu Asp Leu His Lys
Pro Gly Gln Val PAPEP-5 identified in applicants' sequence
listing as sequence no. 6:
Asn Tyr Val Gly Pro Gly Asn Glu Leu Gln
Ala Gly Pro Pro Gln Ser Ala Val Asp Ser
Ala Ala Arg Ile His Asp Phe Arg Tyr Ser
Gln Leu PAPEP-6 identified in applicants' sequence
listing as sequence no. 7:
Pro Tyr Thr His Trp Thr Val Ala Asp Glu
Glu Leu Leu Lys Asn Ile Lys Asn Glu Thr
Gly Phe PAPEP-7 identified in applicants' sequence
listing as sequence no. 8:
Asn Ala Ser Glu Lys Tyr Pro Ser Met Thr
Ser Val Asn Ser Ala Glu Ala Ser PAPEP-8 identified in applicants' sequence
listing as sequence no. 1:
Asn Pro Tyr Thr His Trp Thr Val Ala Asp
Glu Glu Leu Leu Lys His Ile Lys
```

These antigens can be prepared in large quantities by synthesis without problems, purified and then employed in the ELISA in concentrations between 100–200 ng per mixture.

Even when good results can be achieved with just one of the peptides, conjoint use of two or three peptides is preferred.

It is possible to use for detecting IgG or IgM antibodies in some cases different peptides or combinations thereof.

EXAMPLE 4 a) Determination of Serum Antibodies Against Parvovirus B19

The antigens purified and described in Example 2 were used to test a relatively large quantity of sera for their reactivity with these antigens. For this, the various recombinant proteins were added in a concentration of 0.5–1 $\mu$g/ml in carbonate buffer, pH 9.5, to the wells of commercially available ELISA plates for 16 h for binding on. After unbound material has been washed out it is possible then to store these plates in the dry state at 4° C.

Incubation with the sera for 2 h took place in a dilution of 1:100, and the subsequent washing procedures and the detection of bound antibodies with a peroxidase-coupled anti-human IgG antibody took place by conventional test procedures.

Various serum panels were tested for anti-B19 IgG:

1. Sera from a patient with acute B19 infection were investigated consecutively from the appearance of erythema infectiosum up to 19 weeks after the illness.

Result:

All the sera were recognised as anti-B19 IgG positive even from the start of the clinical manifestation and remained positive over the observation period (19 weeks) both with the fusion protein from pGEX1PAN (PCE, see Example 2) and with a VP-1 region cleaved off by BrCN (PAN-1, see Example 2) and with a VP1 portion cleaved off by thrombin (PAN-4) too as antigens.

2. Serum pairs from pregnant women (n=21) from whom a serum sample was taken on hospitalisation and four weeks later were tested for anti-B19 IgG. The same sera were used for each antigen.

Result:

PCE:

Of the 21 pregnant women, 15 were anti-B19 negative and 6 were anti-B19 IgG positive at the time of hospitalisation. The serological result on the second serum sample four weeks later produced an identical result.

PAN-2:

Of the 21 pregnant women, 14 were anti-B19 IgG negative and 7 were anti-B19 positive at the time of hospitalisation. On retesting serum samples taken from these women four weeks later, IgG was no longer detectable in one woman who was previously anti-B19 IgG positive.

PAN-4:

Of the 21 pregnant women, 15 were anti-B19 negative and 6 were anti-B19 IgG positive at the time of hospitalisation. The serological result on the second serum sample four weeks later produced an identical result.

b) Testing of a Definitely B19 IgG/M-positive/negative Serum Collection (n=13)

The sera used were obtained from clinically defined cases and had previously been checked in an IgG/M test which uses purified virus as antigen. Sera 1–6: anti-B19 negative, 7–9: IgM/IgG-positive, 10–13; IgM-negative, IgG-positive.

PAN-4 were tested by the procedure described above. The IgM antibodies were determined by the same test principle as for the IgG determination but PANSE and PAV-1-B were bound as antigens to the plates in a 1:1 mixture with a 10-fold higher concentration, furthermore the serum IgG antibodies were eliminated by pre-adsorption with protein A-coupled beads.

The following values for the absorption were obtained:

IgG determination with PAN-4 (about 20 ng per test well), IgM with a 1:1 mixture of PANSE and PAV-1-B (about 150 ng per test well total protein)

| Serum | IgG | IgM |
| --- | --- | --- |
| 1 | 0.09 | 0.07 |
| 2 | 0.05 | 0.06 |
| 3 | 0.10 | 0.08 |
| 4 | 0.07 | 0.06 |
| 5 | 0.07 | 0.08 |
| 6 | 0.04 | 0.07 |
| 7 | 1.82 | 1.53 |
| 8 | 0.90 | 0.46 |
| 9 | 0.72 | 0.56 |
| 10 | 1.10 | 0.08 |
| 11 | 0.62 | 0.14 |
| 12 | 0.98 | 0.11 |
| 13 | 0.87 | 0.09 |

The results show a clear discrimination of the positive/negative sera both for the IgG test and for the IgM test.

The IgM-positive sera used were obtained from clinically defined cases and had previously been checked in an IgM test which uses purified virus as antigen. A test mixture with recombinant antigens from the VP1 and VP2 regions also recognised all IgM-positive sera. It emerged that the "PAPST, VP2 but especially PANSE" VP2 portions reacted better in this case than in the IgG test. Both regions will therefore be represented in a commercial test kit for IgM.

A further improvement in the sensitivity can be achieved by selectively binding the serum IgM antibodies to the solid phase by means of monoclonal antibodies, adding recombinant antigen (baculovirus-expressed particulate VP-2) and determining the binding ($\mu$-capture assay).

These experiments demonstrate the high reliability of the test carried out using the immunologically active polypeptides according to the invention.

The VP2 region contained in the antigens called "PANSE, PAPST and VP-2" results in no additional increase in the sensitivity for the determination of antibodies from patients with long-passed infection. On the other hand, a good reaction with these antigens is to be found in the case of sera within infection only in the recent past. This antigen is therefore suitable for providing information about the timing of the infection.

In a test kit it is possible to admix one or a mixture of these antigens either with the VP1 portions produced by genetic engineering or with the synthetic peptide, or else to use these in separate mixtures where the discrimination of the reactivity with these two regions provides additional information about the timing of the infection.

A further improvement in the sensitivity can be achieved by selective binding of the serum IgM antibodies to the solid phase by means of monoclonal antibodies, adding recombinant antigen and determining the binding ($\mu$-capture assay).

EXAMPLE 5

Use of B19-specific DNA Primers for Direct Detection of Pathogen

Any B19 DNA present were obtained from the investigation samples (serum, biopsies) by proteinase K digestion in the presence of 1% SDS (2 h, 37° C.), phenol extraction and precipitation in 70% ethanol. This, and the DNA amplification which then followed too, was carried out in analogy to the procedure described in Example 1. Primers O-5 and O-2 (see FIG. 1 for the sequence and position on the B19 genome) were usea; in the case of B19-positive samples, the amplified fragment has a size of 319 bp. Demonstration of the B19-specificity of the DNA fragment was carried out after fractionation of the PCR mixtures by a 1.5% agarose gel, transfer of the DNA to a nitrocellulose membrane (Southern blot) and hybridisation with a piece of DNA which was located between them and which had been labelled either radioactively with 32P (sic) or digoxygenin (sic) by conventional methods (primer extension). The DNA fragment used for the hybridisation was obtained in the following way: a DNA fragment 260 bp long was isolated from the plasmid pUC12PAN after digestion with HincII and PstI and inserted into the HincII and PstI sites in pUC12. It is now possible for the B19 fragment without the sequences used for the amplification to be obtained from the resulting plasmid (pUC12PCRDIA) by EcoRI/PstI digestion and be employed after labelling as hybridisation probe.

DESCRIPTION OF THE FIGURES

FIG. 1: Diagrammatic representation of the VP1/2 encoding region of parvovirus B19 with the primer sequences used for the amplification.

Figure 3:
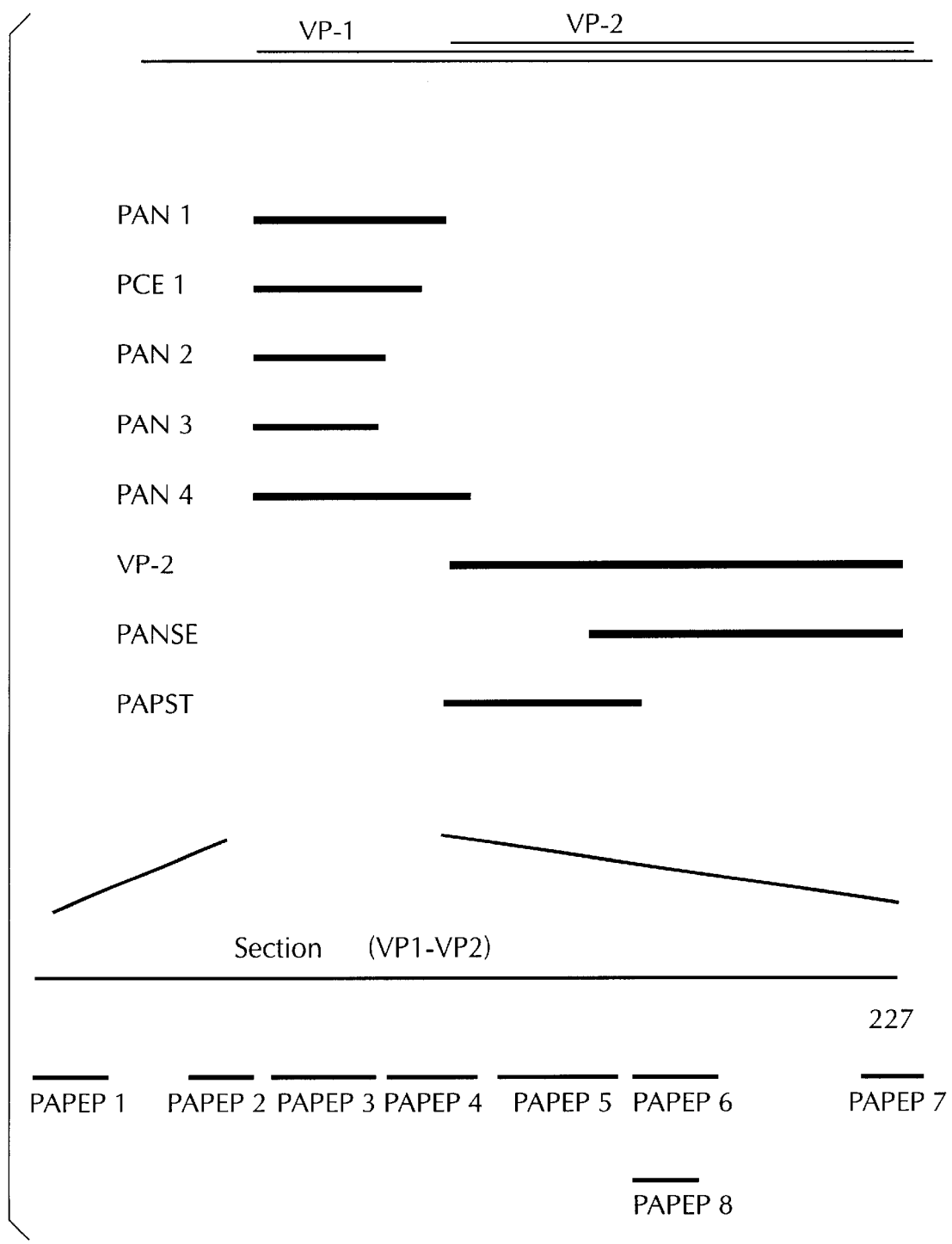

The structure of the single-stranded B19 genome with the inverse regions at the ends (double strand) and with coding regions is depicted diagrammatically in the upper part. The coding region for the non-structural proteins (NS) which are synthesised as polypeptide and then processed is in the left region. The right region codes for the surface proteins of the viral capsid (VP1/2), with VP1 being, apart from an additional N-terminal region (shaded bar), identical to VP2 (black bar). Underneath this are indicated the regions of oligodeoxynucleotides O-1 to O-4 identified in applicants' sequence listing as sequence no. 24, sequence no. 25, sequence no. 26, sequence no. 27 and sequence no. 28, respectively, which were used as primers for the amplification (PCR) of the B19 sequences located between them (O-1 and O-2 for the VP1 region, and O-3 and O-4 for VP-2).

The DNA sequences of the corresponding B19 regions as well as of the oligodeoxynucleotides are indicated in the lower part of the figure. The oligodeoxynucleotide sequences are identified by bold print, non-homologous regions, that is to say sequences which do not hybridise with B19, are contrasted by a line spacing. These non-hybridising sequences represent restriction enzymes sites for EcoRI (GAATTC) and BclI (TGATCA) in the case of O-1, for EcoRI, BclI and BspHII (TC-ATGA) in the case of O-3, and for HindIII (AAGCT-T) in the case of O-4. The amplified VP2 encoding fragment (O-3 and O-4) was digested with EcoRI and HindIII before insertion in pUC vectors, the VP1 encoding fragment with EcoRI and PstI, the PstI cleavage site being located in the B19 DNA (from position no. 4 in the indicated sequence for O-2, CTGCAG).

The oligodeoxynucleotides are identified in Applicants' sequence listing as follows;

O-1 SEQ ID NO: 24
O-2 SEQ ID NO: 25
O-3 SEQ ID NO: 26
O-4 SEQ ID NO: 27
O-5 SEQ ID NO: 28.

FIG. 2: Amino-acid sequences of the antigens described in Example 2 and produced by recombination in *E. coli* cells.

Owing to cloning steps, in each case some non-B19-authentic foreign amino acids are also contained at the N-termini and at the C-termini (apart from PANSE AND (sic) VP-2) and are emphasised by bold print.

The amino-acid sequences of the antigens described in Example 2 are described:

FIG. 2-1: PAN-1 identified in applicants' sequence listing as sequence no. 15;

FIG. 2-2: PCE identified in applicants' sequence listing as sequence no. 9;

FIG. 2-3: PAN-2 identified in applicants' sequence listing as sequence no. 10;

FIG. 2-4: PAN-3 identified in applicants' sequence listing as sequence no. 11;

FIG. 2-5: PAN-4 identified in applicants' sequence listing as sequence no. 12;

FIG. 2-6: VP2 identified in applicants' sequence listing as sequence no. 22;

FIG. 2-6A identified in applicants' sequence listing as sequence no. 18

FIG. 2-6B identified in applicants' sequence listing as sequence no. 19;

FIG. 2-7: PANSE identified in applicants' sequence listing as sequence no. 13;

FIG. 2-7A identified in applicants' sequence listing as sequence no. 20

FIG. 2-7B identified in applicants' sequence listing as sequence no. 21.

FIG. 2-8: PAPST identified in applicants' sequence listing as sequence no. 14;

FIG. 2-9: PAV-1B identified in applicants' sequence listing as sequence no. 16;

FIG. 2-10: PAV-1N identified in applicants' sequence listing as sequence no. 17;

FIG. 3: Diagrammatic representation of the arrangement of some peptides with respect to one another

---

What is claimed is:

1. A test kit for the detection of antibodies against human parvovirus B 19, said test kit comprising:
   A) a peptide or polypeptide consisting of an amino acid sequence selected from the group consisting of:
      i) a partial amino acid sequence consisting of 8 to 50 consecutive amino acid residues of SEQ ID NO.: 15, said partial amino acid sequence being capable of reacting with an antibody specific for the capsid protein VP1 of parvovirus B19; and
      ii) an amino acid sequence selected from the group consisting of SEQ ID NO.: 1, SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 16, SEQ ID NO.: 17, SEQ ID NO.: 18, SEQ ID NO.: 19, SEQ ID NO.: 20, SEQ ID NO.: 21; and SEQ ID NO.: 22; and
   B) at least one indicator which makes it possible to detect a complex of said peptide or polypeptide and an antibody.

2. The test kit according to claim 1, wherein said peptide or polypeptide is biotinylated, and said at least one indicator component is avidin or streptavidin with an enzyme, covalently bonded thereto.

3. The test kit according to claim 2, wherein said enzyme is peroxidase.

4. The test kit according to claim 2, wherein said kit is an ELISA kit.

5. The test kit according to claim 1, further comprising monoclonal antibodies against human IgM antibodies coupled to a microtiter plate, and wherein said peptide or polypeptide is biotinylated, and said at least one indicator is avidin or streptavidin with an enzyme, covalently bonded thereto.

6. The test kit according to claim 5, wherein said enzyme is peroxidase.

7. The test kit according to claim 1, wherein said peptide or polypeptide is coupled to a microtiter plate, and wherein said at least one indicator comprises a label and an antibody able to react with said peptide or polypeptide.

8. The test kit according to claim 7, wherein said label is a radioactive isotope.

9. The test kit according to claim 7, wherein said label is an enzyme which is able to catalyze a color reaction.

10. The test kit according to claim 7, wherein said label is an enzyme and said kit is an ELISA kit.

11. The test kit of claim 1 wherein the polypeptide is a partial sequence of 10 to 32 amino-acid residues of the peptide SEQ ID NO.:15.

12. The test kit according to claim 1, wherein said amino acid sequence is SEQ ID NO.:20.

13. The test kit according to claim 1, wherein said amino acid sequence is SEQ ID NO.:22.

14. The test kit according to claim 1, wherein said amino acid sequence is SEQ ID NO.:10.

15. The test kit according to claim 1, wherein said amino acid sequence is SEQ ID NO.:13.

16. The test kit according to claim 1, wherein said at least one indicator comprises a label and an antibody which is directed against the antibody of said complex to be detected.

17. The test kit according to claim 16, wherein said label is a radioactive isotope.

18. The test kit according to claim 16, wherein said label is an enzyme which is able to catalyze a color reaction.

19. The test kit according to claim 18, wherein said kit is an ELISA kit.

20. The test kit according to claim 19, wherein said peptide or polypeptide is coupled to a microtiter plate, and said at least one indicator comprises an anti-human IgG and/or IgM antibody and an enzyme which is able to catalyze a color reaction, covalently bonded thereto.

* * * * *

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
      (A) LENGTH: 18
      (B) TYPE: AMINO ACID
      (C) TOPOLOGY: LINEAR (ii) MOLECULE TYPE:
      (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE INFECTION (ERYTHEMA INFECTIOSUM)

(vii) IMMEDIATE SOURCE: SYNTHESIZED PEPTIDE (viii) POSITION IN GENOME: N/A

```
    (ix) FEATURE:
         (A) NAME/KEY:
         (B) LOCATION:
         (C) IDENTIFICATION METHOD: amino acid analysis and
             mass spectrometry
         (D) OTHER INFORMATION:

(x) PUBLICATION INFORMATION:
         (A) AUTHORS: COSSART, Y.E.
                      FIELD, A.M.
                      CANT, B.
                      WIDDOWS, D.
         (B) TITLE: PARVOVIRUS-LIKE PARTICLES IN HUMAN SERA
         (C) JOURNAL: LANCET
         (D) VOLUME: I
         (E) ISSUE:
         (F) PAGES: 72-73
         (G) DATE: 1975
         (H) DOCUMENT NUMBER:
         (I) FILING DATE:
         (J) PUBLICATION DATE:
         (K) RELEVANT RESIDUES IN SEQ ID NO: 1:

(xi) PUBLICATION INFORMATION:
         (A) AUTHORS: MANIATIS, T.
                      FRITSCH, E.F.
                      SAMBROOK, J.
         (B) TITLE: MOLECULAR CLONING
         (C) JOURNAL: COLD SPRING HARBOR, NY
         (D) VOLUME:
         (E) ISSUE:
         (F) PAGES:
         (G) DATE: 1982
         (H) DOCUMENT NUMBER:
         (I) FILING DATE:
         (J) PUBLICATION DATE:
         (K) RELEVANT RESIDUES IN SEQ ID NO: 1:

(xii) PUBLICATION INFORMATION:
         (A) AUTHORS: SMITH, D.B.
                      JOHNSON, K.S.
         (B) TITLE: SINGLE STEP PURIFICATION OF POLYPEPTIDES
             EXPRESSED IN ESCHERICHIA COLI AS FUSIONS WITH
             GLUTATHIONE S. TRANSFERASE
         (C) JOURNAL: GENE
         (D) VOLUME:
         (E) ISSUE: 67
         (F) PAGES: 31-40
         (G) DATE: 1988
         (H) DOCUMENT NUMBER:
         (I) FILING DATE:
         (J) PUBLICATION DATE:
         (K) RELEVANT RESIDUES IN SEQ ID NO: 1:

(xiii) SEQUENCE DESCRIPTION: SEQ ID NO: 1:

Asn Pro Tyr Thr His Trp Thr Val Ala Asp Glu Glu Leu leu
1               5                   10

Lys His Ile Lys
15

(2) INFORMATION FOR SEQ ID NO: 2:

(i) SEQUENCE CHARACTERISTICS:
         (A) LENGTH: 19
         (B) TYPE: AMINO ACID
         (C) TOPOLOGY: LINEAR (ii) MOLECULE TYPE:
         (A) DESCRIPTION: PEPTIDE (iii) HYPOTHETICAL: N/A (iv) ANTI-SENSE: N/A (v) FRAGMENT TYPE: INTERNAL
```

(vi) ORIGINAL SOURCE: SERUM FROM PATIENT WITH ACUTE
            INFECTION (ERYTHEMA INFECTIOSUM)

(vii) IMMEDIATE SOURCE: SYNTHESIZED PEPTIDE (viii) POSITION IN GENOME: N/A (ix) FEATURE:
            (A) NAME/KEY:
            (B) LOCATION:
            (C) IDENTIFICATION METHOD: amino acid analysis and
                mass spectrometry
            (D) OTHER INFORMATION:

(x) PUBLICATION INFORMATION:
            (A) AUTHORS: COSSART, Y.E.
                         FIELD, A.M.
                         CANT, B.
                         WIDDOWS, D.
            (B) TITLE: PARVOVIRUS-LIKE PARTICLES IN HUMAN SERA
            (C) JOURNAL: LANCET
            (D) VOLUME: I
            (E) ISSUE:
            (F) PAGES: 72-73
            (G) DATE: 1975
            (H) DOCUMENT NUMBER:
            (I) FILING DATE:
            (J) PUBLICATION DATE:
            (K) RELEVANT RESIDUES IN SEQ ID NO: 2:

(xi) PUBLICATION INFORMATION:
            (A) AUTHORS: MANIATIS, T.
                         FRITSCH, E.F.
                         SAMBROOK, J.
            (B) TITLE: MOLECULAR CLONING
            (C) JOURNAL: COLD SPRING HARBOR, NY
            (D) VOLUME:
            (E) ISSUE:
            (F) PAGES:
            (G) DATE: 1982
            (H) DOCUMENT NUMBER:
            (I) FILING DATE:
            (J) PUBLICATION DATE:
            (K) RELEVANT RESIDUES IN SEQ ID NO: 2:

(xii) PUBLICATION INFORMATION:
            (A) AUTHORS: SMITH, D.B.
                         JOHNSON, K.S.
            (B) TITLE: SINGLE STEP PURIFICATION OF POLYPEPTIDES
                EXPRESSED IN ESCHERICHIA COLI AS FUSIONS WITH
                GLUTATHIONE S. TRANSFERASE
            (C) JOURNAL: GENE
            (D) VOLUME:
            (E) ISSUE: 67
            (F) PAGES: 31-40
            (G) DATE: 1988
            (H) DOCUMENT NUMBER:
            (I) FILING DATE:
            (J) PUBLICATION DATE:
            (K) RELEVANT RESIDUES IN SEQ ID NO: 2:

(xiii) SEQUENCE DESCRIPTION: SEQ ID NO: 2:

Ser Lys Lys Ser Gly Lys Trp Trp Glu Ser Asp Asp Lys Phe
1               5                   10

Ala Lys Ala Val Tyr
15

(2) INFORMATION FOR SEQ ID NO: 3:

(i) SEQUENCE CHARACTERISTICS:
          (A) LENGTH: 18
          (B) TYPE: AMINO ACID
          (C) TOPOLOGY: LINEAR (ii) MOLECULE TYPE:

```
                (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
               INFECTION (ERYTHEMA INFECTIOSUM)

(vii) IMMEDIATE SOURCE: SYNTHESIZED PEPTIDE (viii) POSITION IN GENOME: N/A (ix) FEATURE:
               (A) NAME/KEY:
               (B) LOCATION:
               (C) IDENTIFICATION METHOD: amino acid analysis and
                   mass spectrometry
               (D) OTHER INFORMATION:

(x) PUBLICATION INFORMATION:
               (A) AUTHORS: COSSART, Y.E.
                            FIELD, A.M.
                            CANT, B.
                            WIDDOWS, D.
               (B) TITLE: PARVOVIRUS-LIKE PARTICLES IN HUMAN SERA
               (C) JOURNAL: LANCET
               (D) VOLUME: I
               (E) ISSUE:
               (F) PAGES: 72-73
               (G) DATE: 1975
               (H) DOCUMENT NUMBER:
               (I) FILING DATE:
               (J) PUBLICATION DATE:
               (K) RELEVANT RESIDUES IN SEQ ID NO: 3:

(xi) PUBLICATION INFORMATION:
               (A) AUTHORS: MANIATIS, T.
                            FRITSCH, E.F.
                            SAMBROOK, J.
               (B) TITLE: MOLECULAR CLONING
               (C) JOURNAL: COLD SPRING HARBOR, NY
               (D) VOLUME:
               (E) ISSUE:
               (F) PAGES:
               (G) DATE: 1982
               (H) DOCUMENT NUMBER:
               (I) FILING DATE:
               (J) PUBLICATION DATE:
               (K) RELEVANT RESIDUES IN SEQ ID NO: 3:

(xii) PUBLICATION INFORMATION:
               (A) AUTHORS: SMITH, D.B.
                            JOHNSON, K.S.
               (B) TITLE: SINGLE STEP PURIFICATION OF POLYPEPTIDES
                   EXPRESSED IN ESCHERICHIA COLI AS FUSIONS WITH
                   GLUTATHIONE S. TRANSFERASE
               (C) JOURNAL: GENE
               (D) VOLUME:
               (E) ISSUE: 67
               (F) PAGES: 31-40
               (G) DATE: 1988
               (H) DOCUMENT NUMBER:
               (I) FILING DATE:
               (J) PUBLICATION DATE:
               (K) RELEVANT RESIDUES IN SEQ ID NO: 3:

(xiii) SEQUENCE DESCRIPTION: SEQ ID NO: 3:

Leu Lys Asp His Tyr Asn Ile Ser Leu Asp Asn Pro Leu Glu
1               5                   10

Asn Pro Ser Ser
15

(2) INFORMATION FOR SEQ ID NO: 4:
```

(i) SEQUENCE CHARACTERISTICS:
        (A) LENGTH: 28
        (B) TYPE: AMINO ACID
        (C) TOPOLOGY: LINEAR (ii) MOLECULE TYPE:
        (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
        INFECTION (ERYTHEMA INFECTIOSUM)

(vii) IMMEDIATE SOURCE: SYNTHESIZED PEPTIDE (viii) POSITION IN GENOME: N/A (ix) FEATURE:
        (A) NAME/KEY:
        (B) LOCATION:
        (C) IDENTIFICATION METHOD: amino acid analysis and
            mass spectrometry
        (D) OTHER INFORMATION:

(x) PUBLICATION INFORMATION:
        (A) AUTHORS: COSSART, Y.E.
                     FIELD, A.M.
                     CANT, B.
                     WIDDOWS, D.
        (B) TITLE: PARVOVIRUS-LIKE PARTICLES IN HUMAN SERA
        (C) JOURNAL: LANCET
        (D) VOLUME: I
        (E) ISSUE:
        (F) PAGES: 72-73
        (G) DATE: 1975
        (H) DOCUMENT NUMBER:
        (I) FILING DATE:
        (J) PUBLICATION DATE:
        (K) RELEVANT RESIDUES IN SEQ ID NO: 4:

(xi) PUBLICATION INFORMATION:
        (A) AUTHORS: MANIATIS, T.
                     FRITSCH, E.F.
                     SAMBROOK, J.
        (B) TITLE: MOLECULAR CLONING
        (C) JOURNAL: COLD SPRING HARBOR, NY
        (D) VOLUME:
        (E) ISSUE:
        (F) PAGES:
        (G) DATE: 1982
        (H) DOCUMENT NUMBER:
        (I) FILING DATE:
        (J) PUBLICATION DATE:
        (K) RELEVANT RESIDUES IN SEQ ID NO: 4:

(xii) PUBLICATION INFORMATION:
        (A) AUTHORS: SMITH, D.B.
                     JOHNSON, K.S.
        (B) TITLE: SINGLE STEP PURIFICATION OF POLYPEPTIDES
            EXPRESSED IN ESCHERICHIA COLI AS FUSIONS WITH
            GLUTATHIONE S. TRANSFERASE
        (C) JOURNAL: GENE
        (D) VOLUME:
        (E) ISSUE: 67
        (F) PAGES: 31-40
        (G) DATE: 1988
        (H) DOCUMENT NUMBER:
        (I) FILING DATE:
        (J) PUBLICATION DATE:
        (K) RELEVANT RESIDUES IN SEQ ID NO: 4:

(xiii) SEQUENCE DESCRIPTION: SEQ ID NO: 4:

Ile Lys Asn Asn Leu Lys Asn Ser Pro Asp Leu Tyr Ser His

```
1               5                    10
His Phe Gln Ser His Gly Gln Leu Ser Asp His Pro His Ala
15                   20                   25
```

(2) INFORMATION FOR SEQ ID NO: 5:

(i) SEQUENCE CHARACTERISTICS:
        (A) LENGTH: 24
        (B) TYPE: AMINO ACID
        (C) TOPOLOGY: LINEAR (ii) MOLECULE TYPE:
        (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
        INFECTION (ERYTHEMA INFECTIOSUM)

(vii) IMMEDIATE SOURCE: SYNTHESIZED PEPTIDE (viii) POSITION IN GENOME: N/A (ix) FEATURE:
        (A) NAME/KEY:
        (B) LOCATION:
        (C) IDENTIFICATION METHOD: amino acid analysis and
           mass spectrometry
        (D) OTHER INFORMATION:

(x) PUBLICATION INFORMATION:
        (A) AUTHORS: COSSART, Y.E.
                FIELD, A.M.
                CANT, B.
                WIDDOWS, D.
        (B) TITLE: PARVOVIRUS-LIKE PARTICLES IN HUMAN SERA
        (C) JOURNAL: LANCET
        (D) VOLUME: I
        (E) ISSUE:
        (F) PAGES: 72-73
        (G) DATE: 1975
        (H) DOCUMENT NUMBER:
        (I) FILING DATE:
        (J) PUBLICATION DATE:
        (K) RELEVANT RESIDUES IN SEQ ID NO: 5:

(xi) PUBLICATION INFORMATION:
        (A) AUTHORS: MANIATIS, T.
                FRITSCH, E.F.
                SAMBROOK, J.
        (B) TITLE: MOLECULAR CLONING
        (C) JOURNAL: COLD SPRING HARBOR, NY
        (D) VOLUME:
        (E) ISSUE:
        (F) PAGES:
        (G) DATE: 1982
        (H) DOCUMENT NUMBER:
        (I) FILING DATE:
        (J) PUBLICATION DATE:
        (K) RELEVANT RESIDUES IN SEQ ID NO: 5:

(xii) PUBLICATION INFORMATION:
        (A) AUTHORS: SMITH, D.B.
                JOHNSON, K.S.
        (B) TITLE: SINGLE STEP PURIFICATION OF POLYPEPTIDES
           EXPRESSED IN ESCHERICHIA COLI AS FUSIONS WITH
           GLUTATHIONE S. TRANSFERASE
        (C) JOURNAL: GENE
        (D) VOLUME:
        (E) ISSUE: 67
        (F) PAGES: 31-40
        (G) DATE: 1988
        (H) DOCUMENT NUMBER:

(I) FILING DATE:
            (J) PUBLICATION DATE:
            (K) RELEVANT RESIDUES IN SEQ ID NO: 5:

(xiii) SEQUENCE DESCRIPTION: SEQ ID NO: 5:

Ser Ser His Ala Glu Pro Arg Gly Glu Asn Ala Val Leu Ser
1               5                   10

Ser Glu Asp Leu His Lys Pro Gly Gln Val
15                  20

(2) INFORMATION FOR SEQ ID NO: 6:

(i) SEQUENCE CHARACTERISTICS:
            (A) LENGTH: 32
            (B) TYPE: AMINO ACID
            (C) TOPOLOGY: LINEAR (ii) MOLECULE TYPE:
            (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
            INFECTION (ERYTHEMA INFECTIOSUM)

(vii) IMMEDIATE SOURCE: SYNTHESIZED PEPTIDE (viii) POSITION IN GENOME: N/A (ix) FEATURE:
            (A) NAME/KEY:
            (B) LOCATION:
            (C) IDENTIFICATION METHOD: amino acid analysis and
                mass spectrometry
            (D) OTHER INFORMATION:

(x) PUBLICATION INFORMATION:
            (A) AUTHORS: COSSART, Y.E.
                         FIELD, A.M.
                         CANT, B.
                         WIDDOWS, D.
            (B) TITLE: PARVOVIRUS-LIKE PARTICLES IN HUMAN SERA
            (C) JOURNAL: LANCET
            (D) VOLUME: I
            (E) ISSUE:
            (F) PAGES: 72-73
            (G) DATE: 1975
            (H) DOCUMENT NUMBER:
            (I) FILING DATE:
            (J) PUBLICATION DATE:
            (K) RELEVANT RESIDUES IN SEQ ID NO: 6:

(xi) PUBLICATION INFORMATION:
            (A) AUTHORS: MANIATIS, T.
                         FRITSCH, E.F.
                         SAMBROOK, J.
            (B) TITLE: MOLECULAR CLONING
            (C) JOURNAL: COLD SPRING HARBOR, NY
            (D) VOLUME:
            (E) ISSUE:
            (F) PAGES:
            (G) DATE: 1982
            (H) DOCUMENT NUMBER:
            (I) FILING DATE:
            (J) PUBLICATION DATE:
            (K) RELEVANT RESIDUES IN SEQ ID NO: 6:

(xii) PUBLICATION INFORMATION:
            (A) AUTHORS: SMITH, D.B.
                         JOHNSON, K.S.
            (B) TITLE: SINGLE STEP PURIFICATION OF POLYPEPTIDES
                EXPRESSED IN ESCHERICHIA COLI AS FUSIONS WITH
                GLUTATHIONE S. TRANSFERASE

```
                (C) JOURNAL: GENE
                (D) VOLUME:
                (E) ISSUE: 67
                (F) PAGES: 31-40
                (G) DATE: 1988
                (H) DOCUMENT NUMBER:
                (I) FILING DATE:
                (J) PUBLICATION DATE:
                (K) RELEVANT RESIDUES IN SEQ ID NO: 6:

(xiii) SEQUENCE DESCRIPTION: SEQ ID NO: 6:

Asn Tyr Val Gly Pro Gly Asn Glu Leu Gln Ala Gly Pro Pro
 1               5                  10

Gln Ser Ala Val Asp Ser Ala Ala Arg Ile His Asp Phe Arg
15              20                  25

Tyr Ser Gln Leu
    30

(2) INFORMATION FOR SEQ ID NO: 7:

(i) SEQUENCE CHARACTERISTICS:
             (A) LENGTH: 22
             (B) TYPE: AMINO ACID
             (C) TOPOLOGY: LINEAR (ii) MOLECULE TYPE:
             (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
          INFECTION (ERYTHEMA INFECTIOSUM)

(vii) IMMEDIATE SOURCE: SYNTHESIZED PEPTIDE (viii) POSITION IN GENOME: N/A (ix) FEATURE:
             (A) NAME/KEY:
             (B) LOCATION:
             (C) IDENTIFICATION METHOD: amino acid analysis and
                 mass spectrometry
             (D) OTHER INFORMATION:

(x) PUBLICATION INFORMATION:
             (A) AUTHORS: COSSART, Y.E.
                          FIELD, A.M.
                          CANT, B.
                          WIDDOWS, D.
             (B) TITLE: PARVOVIRUS-LIKE PARTICLES IN HUMAN SERA
             (C) JOURNAL: LANCET
             (D) VOLUME: I
             (E) ISSUE:
             (F) PAGES: 72-73
             (G) DATE: 1975
             (H) DOCUMENT NUMBER:
             (I) FILING DATE:
             (J) PUBLICATION DATE:
             (K) RELEVANT RESIDUES IN SEQ ID NO: 7:

(xi) PUBLICATION INFORMATION:
             (A) AUTHORS: MANIATIS, T.
                          FRITSCH, E.F.
                          SAMBROOK, J.
             (B) TITLE: MOLECULAR CLONING
             (C) JOURNAL: COLD SPRING HARBOR, NY
             (D) VOLUME:
             (E) ISSUE:
             (F) PAGES:
             (G) DATE: 1982
             (H) DOCUMENT NUMBER:
             (I) FILING DATE:
```

```
            (J) PUBLICATION DATE:
            (K) RELEVANT RESIDUES IN SEQ ID NO: 7:

(xii) PUBLICATION INFORMATION:
            (A) AUTHORS: SMITH, D.B.
                         JOHNSON, K.S.
            (B) TITLE: SINGLE STEP PURIFICATION OF POLYPEPTIDES
                EXPRESSED IN ESCHERICHIA COLI AS FUSIONS WITH
                GLUTATHIONE S. TRANSFERASE
            (C) JOURNAL: GENE
            (D) VOLUME:
            (E) ISSUE: 67
            (F) PAGES: 31-40
            (G) DATE: 1988
            (H) DOCUMENT NUMBER:
            (I) FILING DATE:
            (J) PUBLICATION DATE:
            (K) RELEVANT RESIDUES IN SEQ ID NO: 7:

(xiii) SEQUENCE DESCRIPTION: SEQ ID NO: 7:

Pro Tyr Thr His Trp Thr Val Ala Asp Glu Glu Leu Leu Lys
 1               5                  10

Asn Ile Lys Asn Glu Thr Gly Phe
15                  20

(2) INFORMATION FOR SEQ ID NO: 8:

(i) SEQUENCE CHARACTERISTICS:
            (A) LENGTH: 18
            (B) TYPE: AMINO ACID
            (C) TOPOLOGY: LINEAR (ii) MOLECULE TYPE:
            (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
         INFECTION (ERYTHEMA INFECTIOSUM)

(vii) IMMEDIATE SOURCE: SYNTHESIZED PEPTIDE (viii) POSITION IN GENOME: N/A (ix) FEATURE:
            (A) NAME/KEY:
            (B) LOCATION:
            (C) IDENTIFICATION METHOD: amino acid analysis and
                mass spectrometry
            (D) OTHER INFORMATION:

(x) PUBLICATION INFORMATION:
            (A) AUTHORS: COSSART, Y.E.
                         FIELD, A.M.
                         CANT, B.
                         WIDDOWS, D.
            (B) TITLE: PARVOVIRUS-LIKE PARTICLES IN HUMAN SERA
            (C) JOURNAL: LANCET
            (D) VOLUME: I
            (E) ISSUE:
            (F) PAGES: 72-73
            (G) DATE: 1975
            (H) DOCUMENT NUMBER:
            (I) FILING DATE:
            (J) PUBLICATION DATE:
            (K) RELEVANT RESIDUES IN SEQ ID NO: 8:

(xi) PUBLICATION INFORMATION:
            (A) AUTHORS: MANIATIS, T.
                         FRITSCH, E.F.
                         SAMBROOK, J.
            (B) TITLE: MOLECULAR CLONING
```

```
        (C) JOURNAL: COLD SPRING HARBOR, NY
        (D) VOLUME:
        (E) ISSUE:
        (F) PAGES:
        (G) DATE: 1982
        (H) DOCUMENT NUMBER:
        (I) FILING DATE:
        (J) PUBLICATION DATE:
        (K) RELEVANT RESIDUES IN SEQ ID NO: 8:

(xii) PUBLICATION INFORMATION:
        (A) AUTHORS: SMITH, D.B.
                     JOHNSON, K.S.
        (B) TITLE: SINGLE STEP PURIFICATION OF POLYPEPTIDES
            EXPRESSED IN ESCHERICHIA COLI AS FUSIONS WITH
            GLUTATHIONE S. TRANSFERASE
        (C) JOURNAL: GENE
        (D) VOLUME:
        (E) ISSUE: 67
        (F) PAGES: 31-40
        (G) DATE: 1988
        (H) DOCUMENT NUMBER:
        (I) FILING DATE:
        (J) PUBLICATION DATE:
        (K) RELEVANT RESIDUES IN SEQ ID NO: 8:

(xiii) SEQUENCE DESCRIPTION: SEQ ID NO: 8:

Asn Ala Ser Glu Lys Tyr Pro Ser Met Thr Ser Val Asn Ser
1               5                   10

Ala Glu Ala Ser
15

(2) INFORMATION FOR SEQ ID NO: 9:

(i) SEQUENCE CHARACTERISTICS:
        (A) LENGTH: 210
        (B) TYPE: AMINO ACID
        (C) TOPOLOGY: LINEAR (ii) MOLECULE TYPE:
        (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
        INFECTION (ERYTHEMA INFECTIOSUM)

(vii) IMMEDIATE SOURCE: GENETICALLY ENGINEERED PEPTIDE (viii) POSITION IN GENOME: N/A (ix) FEATURE:
        (A) NAME/KEY:
        (B) LOCATION:
        (C) IDENTIFICATION METHOD: amino acid analysis and
            mass spectrometry
        (D) OTHER INFORMATION:

(x) PUBLICATION INFORMATION:
        (A) AUTHORS: OSSART, Y.E.
                     FIELD, A.M.
                     CANT, B.
                     WIDDOWS, D.
        (B) TITLE: PARVOVIRUS-LIKE PARTICLES IN HUMAN SERA
        (C) JOURNAL: LANCET
        (D) VOLUME:
        (E) ISSUE:
        (F) PAGES: 72-73
        (G) DATE: 1975
        (H) DOCUMENT NUMBER:
        (I) FILING DATE:
        (J) PUBLICATION DATE:
```

(K) RELEVANT RESIDUES IN SEQ ID NO: 9:

(xi) PUBLICATION INFORMATION:
            (A) AUTHORS: ANIATIS, T.
                         FRITSCH, E.F.
                         SAMBROOK, J.
            (B) TITLE: MOLECULAR CLONING
            (C) JOURNAL: COLD SPRING HARBOR, NY
            (D) VOLUME:
            (E) ISSUE:
            (F) PAGES:
            (G) DATE: 1982
            (H) DOCUMENT NUMBER:
            (I) FILING DATE:
            (J) PUBLICATION DATE:
            (K) RELEVANT RESIDUES IN SEQ ID NO: 9:

(xii) PUBLICATION INFORMATION:
            (A) AUTHORS: SMITH, D.B.
                         JOHNSON, K.S.
            (B) TITLE: SINGLE STEP PURIFICATION OF POLYPEPTIDES
                EXPRESSED IN ESCHERICHIA COLI AS FUSIONS WITH
                GLUTATHIONE S. TRANSFERASE
            (C) JOURNAL: GENE
            (D) VOLUME:
            (E) ISSUE: 67
            (F) PAGES: 31-40
            (G) DATE: 1988
            (H) DOCUMENT NUMBER:
            (I) FILING DATE:
            (J) PUBLICATION DATE:
            (K) RELEVANT RESIDUES IN SEQ ID NO: 9:

(xiii) SEQUENCE DESCRIPTION: SEQ ID NO: 9:

His Met Ser Lys Lys Ser Gly Lys Trp Trp Glu Ser Asp Asp
 1               5                  10

Lys Phe Ala Lys Ala Val Tyr Gln Gln Phe Val Glu Phe Tyr
15                  20                      25

Glu Lys Val Thr Gly Thr Asp Leu Glu Leu Ile Gln Ile Leu
       30              35                  40

Lys Asp His Tyr Asn Ile Ser Leu Asp Asn Pro Leu Glu Asn
           45                  50              55

Pro Ser Ser Leu Phe Asp Leu Val Ala Arg Ile Lys Asn Asn
               60                  65              70

Leu Lys Asn Ser Pro Asp Leu Tyr Ser His His Phe Gln Ser
                   75                  80

His Gly Gln Leu Ser Asp His Pro His Ala Leu Ser Ser Ser
85                  90                  95

Ser Ser His Ala Glu Pro Arg Gly Glu Asn Ala Val Leu Ser
        100             105                 110

Ser Glu Asp Leu His Lys Pro Gly Gln Val Ser Val Gln Leu
            115                 120                 125

Pro Gly Thr Asn Tyr Val Gly Pro Gly Asn Glu Leu Gln Ala
                130                 135                 140

Gly Pro Pro Gln Ser Ala Val Asp Ser Ala Ala Arg Ile His
                    145                 150

Asp Phe Arg Tyr Ser Gln Leu Ala Lys Leu Gly Ile Asn Pro
155                 160                 165

Tyr Thr His Trp Thr Val Ala Asp Glu Glu Leu Leu Lys Asn
        170                 175                 180

Ile Lys Asn Glu Thr Gly Phe Gln Ala Gln Val Val Lys Asp
            185                 190                 195

Tyr Phe Thr Leu Lys Gly Ala Gly Glu Phe Ile Val Thr Asp
                200                 205                 210

(2) INFORMATION FOR SEQ ID NO: 10:

(i) SEQUENCE CHARACTERISTICS:
      (A) LENGTH: 163
      (B) TYPE: AMINO ACID
      (C) TOPOLOGY: LINEAR (ii) MOLECULE TYPE:
      (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
      INFECTION (ERYTHEMA INFECTIOSUM)

(vii) IMMEDIATE SOURCE: GENETICALLY ENGINEERED PEPTIDE (viii) POSITION IN GENOME: N/A (ix) FEATURE:
      (A) NAME/KEY:
      (B) LOCATION:
      (C) IDENTIFICATION METHOD: amino acid analysis and
         mass spectrometry
      (D) OTHER INFORMATION:

(x) PUBLICATION INFORMATION:
      (A) AUTHORS: COSSART, Y.E.
              FIELD, A.M.
              CANT, B.
              WIDDOWS, D.
      (B) TITLE: PARVOVIRUS-LIKE PARTICLES IN HUMAN SERA
      (C) JOURNAL: LANCET
      (D) VOLUME: I
      (E) ISSUE:
      (F) PAGES: 72-73
      (G) DATE: 1975
      (H) DOCUMENT NUMBER:
      (I) FILING DATE:
      (J) PUBLICATION DATE:
      (K) RELEVANT RESIDUES IN SEQ ID NO: 10:

(xi) PUBLICATION INFORMATION:
      (A) AUTHORS: MANIATIS, T.
              FRITSCH, E.F.
              SAMBROOK, J.
      (B) TITLE: MOLECULAR CLONING
      (C) JOURNAL: COLD SPRING HARBOR, NY
      (D) VOLUME:
      (E) ISSUE:
      (F) PAGES:
      (G) DATE: 1982
      (H) DOCUMENT NUMBER:
      (I) FILING DATE:
      (J) PUBLICATION DATE:
      (K) RELEVANT RESIDUES IN SEQ ID NO: 10:

(xii) PUBLICATION INFORMATION:
      (A) AUTHORS: SMITH, D.B.
              JOHNSON, K.S.
      (B) TITLE: SINGLE STEP PURIFICATION OF POLYPEPTIDES
         EXPRESSED IN ESCHERICHIA COLI AS FUSIONS WITH
         GLUTATHIONE S. TRANSFERASE
      (C) JOURNAL: GENE
      (D) VOLUME:
      (E) ISSUE: 67
      (F) PAGES: 31-40
      (G) DATE: 1988
      (H) DOCUMENT NUMBER:
      (I) FILING DATE:
      (J) PUBLICATION DATE:
      (K) RELEVANT RESIDUES IN SEQ ID NO: 10:

-continued (xiii) SEQUENCE DESCRIPTION: SEQ ID NO: 10:

```
Gly Ser Arg Arg Pro Asp His Met Ser Lys Lys Ser Gly Lys
1               5                   10
Trp Trp Glu Ser Asp Asp Lys Phe Ala Lys Ala Val Tyr Gln
15                  20                  25
Gln Phe Val Glu Phe Tyr Glu Lys Val Thr Gly Thr Asp Leu
    30                  35                  40
Glu Leu Ile Gln Ile Leu Lys Asp His Tyr Asn Ile Ser Leu
        45                  50                  55
Asp Asn Pro Leu Glu Asn Pro Ser Ser Leu Phe Asp Leu Val
            60                  65                  70
Ala Arg Ile Lys Asn Asn Leu Lys Asn Ser Pro Asp Leu Tyr
                75                  80
Ser His His Phe Gln Ser His Gly Gln Leu Ser Asp His Pro
85              90                  95
His Ala Leu Ser Ser Ser Ser Ser His Ala Glu Pro Arg Gly
    100                 105                 110
Glu Asn Ala Val Leu Ser Ser Glu Asp Leu His Lys Pro Gly
        115                 120                 125
Gln Val Ser Val Gln Leu Pro Gly Thr Asn Tyr Val Gly Pro
            130                 135                 140
Gly Asn Glu Leu Gln Ala Gly Pro Pro Gln Ser Ala Val Gly
                145                 150
Asp Pro Arg Glu Phe Ile Val Thr Asp
155                 160
```

(2) INFORMATION FOR SEQ ID NO: 11:

(i) SEQUENCE CHARACTERISTICS:
      (A) LENGTH: 169
      (B) TYPE: AMINO ACID
      (C) TOPOLOGY: LINEAR (ii) MOLECULE TYPE:
      (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
      INFECTION (ERYTHEMA INFECTIOSUM)

(vii) IMMEDIATE SOURCE: GENETICALLY ENGINEERED PEPTIDE (viii) POSITION IN GENOME: N/A (ix) FEATURE:
      (A) NAME/KEY:
      (B) LOCATION:
      (C) IDENTIFICATION METHOD: amino acid analysis and
         mass spectrometry
      (D) OTHER INFORMATION:

(x) PUBLICATION INFORMATION:
      (A) AUTHORS: COSSART, Y.E.
              FIELD, A.M.
              CANT, B.
              WIDDOWS, D.
      (B) TITLE: PARVOVIRUS-LIKE PARTICLES IN HUMAN SERA
      (C) JOURNAL: LANCET
      (D) VOLUME: I
      (E) ISSUE:
      (F) PAGES: 72-73

```
            (G) DATE: 1975
            (H) DOCUMENT NUMBER:
            (I) FILING DATE:
            (J) PUBLICATION DATE:
            (K) RELEVANT RESIDUES IN SEQ ID NO: 11:

(xi) PUBLICATION INFORMATION:
            (A) AUTHORS: MANIATIS, T.
                        FRITSCH, E.F.
                        SAMBROOK, J.
            (B) TITLE: MOLECULAR CLONING
            (C) JOURNAL: COLD SPRING HARBOR, NY
            (D) VOLUME:
            (E) ISSUE:
            (F) PAGES:
            (G) DATE: 1982
            (H) DOCUMENT NUMBER:
            (I) FILING DATE:
            (J) PUBLICATION DATE:
            (K) RELEVANT RESIDUES IN SEQ ID NO: 11:

(xii) PUBLICATION INFORMATION:
            (A) AUTHORS: SMITH, D.B.
                        JOHNSON, K.S.
            (B) TITLE: SINGLE STEP PURIFICATION OF POLYPEPTIDES
                EXPRESSED IN ESCHERICHIA COLI AS FUSIONS WITH
                GLUTATHIONE S. TRANSFERASE
            (C) JOURNAL: GENE
            (D) VOLUME:
            (E) ISSUE: 67
            (F) PAGES: 31-40
            (G) DATE: 1988
            (H) DOCUMENT NUMBER:
            (I) FILING DATE:
            (J) PUBLICATION DATE:
            (K) RELEVANT RESIDUES IN SEQ ID NO: 11:

(xiii) SEQUENCE DESCRIPTION: SEQ ID NO: 11:

Gly Ile Leu Ser Arg Arg Pro Asp His Met Ser Lys Lys Ser
1               5                   10

Gly Lys Trp Trp Glu Ser Asp Asp Lys Phe Ala Lys Ala Val
15                  20                  25

Tyr Gln Gln Phe Val Glu Phe Tyr Glu Lys Val Thr Gly Thr
        30                  35                  40

Asp Leu Glu Leu Ile Gln Ile Leu Lys Asp His Tyr Asn Ile
            45                  50                  55

Ser Leu Asp Asn Pro Leu Glu Asn Pro Ser Ser Leu Phe Asp
                60                  65                  70

Leu Val Ala Arg Ile Lys Asn Asn Leu Lys Asn Ser Pro Asp
                    75                  80

Leu Tyr Ser His His Phe Gln Ser His Gly Gln Leu Ser Asp
85                  90                  95

His Pro His Ala Leu Ser Ser Ser Ser His Ala Glu Pro
        100                 105                 110

Arg Gly Glu Asn Ala Val Leu Ser Ser Glu Asp Leu His Lys
            115                 120                 125

Pro Gly Gln Val Ser Val Gln Leu Pro Gly Thr Asn Tyr Val
                130                 135                 140

Gly Pro Gly Asn Glu Leu Gln Ala Gly Pro Pro Gln Ser Ala
                    145                 150

Val Gly Asp Pro Leu Glu Asp Pro Arg Val Pro Ser Ser Asn
155                 160                 165

Ser (2) INFORMATION FOR SEQ ID NO: 12:
```

```
      (i) SEQUENCE CHARACTERISTICS:
          (A) LENGTH: 250
          (B) TYPE: AMINO ACID
          (C) TOPOLOGY: LINEAR (ii) MOLECULE TYPE:
          (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
          NFECTION (ERYTHEMA INFECTIOSUM)

(vii) IMMEDIATE SOURCE: GENETICALLY ENGINEERED PEPTIDE (viii) POSITION IN GENOME: N/A (ix) FEATURE:
          (A) NAME/KEY: N/A
          (B) LOCATION: N/A
          (C) IDENTIFICATION METHOD: amino acid analysis and
              mass spectrometry
          (D) OTHER INFORMATION:

(x) PUBLICATION INFORMATION:
          (A) AUTHORS: COSSART, Y.E.
                       FIELD, A.M.
                       CANT, B.
                       WIDDOWS, D.
          (B) TITLE: PARVOVIRUS-LIKE PARTICLES IN HUMAN SERA
          (C) JOURNAL: LANCET
          (D) VOLUME: I
          (E) ISSUE:
          (F) PAGES: 72-73
          (G) DATE: 1975
          (H) DOCUMENT NUMBER:
          (I) FILING DATE:
          (J) PUBLICATION DATE:
          (K) RELEVANT RESIDUES IN SEQ ID NO: 12:

(xi) PUBLICATION INFORMATION:
          (A) AUTHORS: MANIATIS, T.
                       FRITSCH, E.F.
                       SAMBROOK, J.
          (B) TITLE: MOLECULAR CLONING
          (C) JOURNAL: COLD SPRING HARBOR, NY
          (D) VOLUME:
          (E) ISSUE:
          (F) PAGES:
          (G) DATE: 1982
          (H) DOCUMENT NUMBER:
          (I) FILING DATE:
          (J) PUBLICATION DATE:
          (K) RELEVANT RESIDUES IN SEQ ID NO: 12:

(xii) PUBLICATION INFORMATION:
          (A) AUTHORS: SMITH, D.B.
                       JOHNSON, K.S.
          (B) TITLE: SINGLE STEP PURIFICATION OF POLYPEPTIDES
              EXPRESSED IN ESCHERICHIA COLI AS FUSIONS WITH
              GLUTATHIONE S. TRANSFERASE
          (C) JOURNAL: GENE
          (D) VOLUME:
          (E) ISSUE: 67
          (F) PAGES: 31-40
          (G) DATE: 1988
          (H) DOCUMENT NUMBER:
          (I) FILING DATE:
          (J) PUBLICATION DATE:
          (K) RELEVANT RESIDUES IN SEQ ID NO: 12:

(xiii) SEQUENCE DESCRIPTION: SEQ ID NO: 12:

Gly Ser Arg Arg Pro Asp His Met Ser Lys Lys Ser Gly Lys
```

```
1               5                   10
Trp Trp Glu Ser Asp Asp Lys Phe Ala Lys Ala Val Tyr Gln
15                  20                  25

Gln Phe Val Glu Phe Tyr Glu Lys Val Thr Gly Thr Asp Leu
        30                  35                  40

Glu Leu Ile Gln Ile Leu Lys Asp His Tyr Asn Ile Ser Leu
            45                  50                  55

Asp Asn Pro Leu Glu Asn Pro Ser Ser Leu Phe Asp Leu Val
                60                  65                  70

Ala Arg Ile Lys Asn Asn Leu Lys Asn Ser Pro Asp Leu Tyr
                    75                  80

Ser His His Phe Gln Ser His Gly Gln Leu Ser Asp His Pro
85                  90                  95

His Ala Leu Ser Ser Ser Ser Ser His Ala Glu Pro Arg Gly
        100                 105                 110

Glu Asn Ala Val Leu Ser Ser Glu Asp Leu His Lys Pro Gly
            115                 120                 125

Gln Val Ser Val Gln Leu Pro Gly Thr Asn Tyr Val Gly Pro
                130                 135                 140

Gly Asn Glu Leu Gln Ala Gly Pro Pro Gln Ser Ala Val Asp
                    145                 150

Ser Ala Ala Arg Ile His Asp Phe Arg Tyr Ser Gln Leu Ala
155                 160                 165

Lys Leu Gly Ile Asn Pro Tyr Thr His Trp Thr Val Ala Asp
        170                 175                 180

Glu Glu Leu Leu Lys Asn Ile Lys Asn Glu Thr Gly Phe Gln
            185                 190                 195

Ala Gln Val Val Lys Asp Tyr Phe Thr Leu Lys Gly Ala Ala
                200                 205                 210

Ala Pro Val Ala His Phe Gln Gly Ser Leu Pro Glu Val Pro
                    215                 220

Ala Tyr Asn Ala Ser Glu Lys Tyr Pro Ser Met Thr Ser Val
225                 230                 235

Asn Ser Ala Gly Arg Arg Ile Pro Gly Asn Ser Ser
        240                 245                 250

(2) INFORMATION FOR SEQ ID NO: 13:

(i) SEQUENCE CHARACTERISTICS:
        (A) LENGTH: 395
        (B) TYPE: AMINO ACID
        (C) TOPOLOGY: LINEAR (ii) MOLECULE TYPE:
        (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
        INFECTION (ERYTHEMA INFECTIOSUM)

(vii) IMMEDIATE SOURCE: GENETICALLY ENGINEERED PEPTIDE (viii) POSITION IN GENOME: N/A (ix) FEATURE:
        (A) NAME/KEY: N/A
```

(B) LOCATION: N/A
            (C) IDENTIFICATION METHOD: amino acid analysis and
                mass spectrometry
            (D) OTHER INFORMATION:

(x) PUBLICATION INFORMATION:
            (A) AUTHORS: COSSART, Y.E.
                         FIELD, A.M.
                         CANT, B.
                         WIDDOWS, D.
            (B) TITLE: PARVOVIRUS-LIKE PARTICLES IN HUMAN SERA
            (C) JOURNAL: LANCET
            (D) VOLUME:
            (E) ISSUE:
            (F) PAGES: 72-73
            (G) DATE: 1975
            (H) DOCUMENT NUMBER:
            (I) FILING DATE:
            (J) PUBLICATION DATE:
            (K) RELEVANT RESIDUES IN SEQ ID NO: 13:

(xi) PUBLICATION INFORMATION:
            (A) AUTHORS: MANIATIS, T.
                         FRITSCH, E.F.
                         SAMBROOK, J.
            (B) TITLE: MOLECULAR CLONING
            (C) JOURNAL: COLD SPRING HARBOR, NY
            (D) VOLUME:
            (E) ISSUE:
            (F) PAGES:
            (G) DATE: 1982
            (H) DOCUMENT NUMBER:
            (I) FILING DATE:
            (J) PUBLICATION DATE:
            (K) RELEVANT RESIDUES IN SEQ ID NO: 13:

(xii) PUBLICATION INFORMATION:
            (A) AUTHORS: SMITH, D.B.
                         JOHNSON, K.S.
            (B) TITLE: SINGLE STEP PURIFICATION OF POLYPEPTIDES
                EXPRESSED IN ESCHERICHIA COLI AS FUSIONS WITH
                GLUTATHIONE S. TRANSFERASE
            (C) JOURNAL: GENE
            (D) VOLUME:
            (E) ISSUE: 67
            (F) PAGES: 31-40
            (G) DATE: 1988
            (H) DOCUMENT NUMBER:
            (I) FILING DATE:
            (J) PUBLICATION DATE:
            (K) RELEVANT RESIDUES IN SEQ ID NO: 13:

(xiii) SEQUENCE DESCRIPTION: SEQ ID NO: 13:

Met Thr Met Ile Thr Pro Ser Leu His Ala Cys Met Leu Val
1               5                   10

Asp His Glu Tyr Lys Tyr Pro Tyr Val Leu Gly Gln Gly Gln
15                  20                  25

Asp Thr Leu Ala Pro Glu Leu Pro Ile Trp Val Tyr Phe Pro
            30                  35                  40

Pro Gln Tyr Ala Tyr Leu Thr Val Gly Asp Val Asn Thr Gln
        45                  50                  55

Gly Ile Ser Gly Asp Ser Lys Lys Leu Ala Ser Glu Glu Ser
            60                  65                  70

Ala Phe Tyr Val Leu Glu His Ser Ser Phe Gln Leu Leu Gly
                75                  80

Thr Gly Gly Thr Ala Ser Met Ser Tyr Lys Phe Pro Pro Val
85                  90                  95

Pro Pro Glu Asn Leu Glu Gly Cys Ser Gln His Phe Tyr Glu
        100                 105                 110

Met Tyr Asn Pro Leu Tyr Gly Ser Arg Leu Gly Val Pro Asp

```
                    115                 120                 125
Thr Leu Gly Gly Asp Pro Lys Phe Arg Ser Leu Thr His Glu
            130                 135                 140
Asp His Ala Ile Gln Pro Gln Asn Phe Met Pro Gly Pro Leu
                145                 150
Val Asn Ser Val Ser Thr Lys Glu Gly Asp Ser Ser Asn Thr
155                 160                 165
Gly Ala Gly Lys Ala Leu Thr Gly Leu Ser Thr Gly Thr Ser
170                 175                 180
Gln Asn Thr Arg Ile Ser Leu Arg Pro Gly Pro Val Ser Gln
            185                 190                 195
Pro Tyr His His Trp Asp Thr Asp Lys Tyr Val Thr Gly Ile
                200                 205                 210
Asn Ala Ile Ser His Gly Gln Thr Thr Tyr Gly Asn Ala Glu
            215                 220
Asp Lys Glu Tyr Gln Gln Gly Val Gly Arg Phe Pro Asn Glu
225                 230                 235
Lys Glu Gln Leu Lys Gln Leu Gln Gly Leu Asn Met His Thr
    240                 245                 250
Tyr Phe Pro Asn Lys Gly Thr Gln Gln Tyr Thr Asp Gln Ile
            255                 260                 265
Glu Arg Pro Leu Met Val Gly Ser Val Trp Asn Arg Arg Ala
                270                 275                 280
Leu His Tyr Glu Ser Gln Leu Trp Ser Lys Ile Pro Asn Leu
                285                 290
Asp Asp Ser Phe Lys Thr Gln Phe Ala Ala Leu Gly Gly Trp
295                 300                 305
Gly Leu His Gln Pro Pro Gln Ile Phe Leu Lys Gln Tyr
    310                 315                 320
Ala Val Gly Ile Met Thr Val Thr Met Thr Phe Lys Leu Gly
            325                 330                 335
Pro Arg Lys Ala Thr Gly Arg Trp Asn Pro Gln Pro Gly Val
                340                 345                 350
Tyr Pro Pro His Ala Ala Gly His Leu Pro Tyr Val Leu Tyr
                355                 360
Asp Pro Thr Ala Thr Asp Ala Lys Gln His His Arg His Gly
365                 370                 375
Tyr Glu Lys Pro Glu Glu Leu Trp Thr Ala Lys Ser Arg Val
    380                 385                 390
His Pro Leu
    395

(2) INFORMATION FOR SEQ ID NO: 14:

(i) SEQUENCE CHARACTERISTICS:
        (A) LENGTH: 264
        (B) TYPE: AMINO ACID
        (C) TOPOLOGY: LINEAR (ii) MOLECULE TYPE:
         (A) DESCRIPTION: PEPTIDE (iii) HYPOTHETICAL: N/A (iv) ANTI-SENSE: N/A (v) FRAGMENT TYPE: INTERNAL
```

(vi) ORIGINAL SOURCE: SERUM FROM PATIENT WITH ACUTE
             INFECTION (ERYTHEMA INFECTIOSUM)

(vii) IMMEDIATE SOURCE: GENETICALLY ENGINEERED PEPTIDE (viii) POSITION IN GENOME: N/A (ix) FEATURE:
             (A) NAME/KEY: N/A
             (B) LOCATION: N/A
             (C) IDENTIFICATION METHOD: amino acid analysis and
                 mass spectrometry
             (D) OTHER INFORMATION:

(x) PUBLICATION INFORMATION:
             (A) AUTHORS: COSSART, Y.E.
                          FIELD, A.M.
                          CANT, B.
                          WIDDOWS, D.
             (B) TITLE: PARVOVIRUS-LIKE PARTICLES IN HUMAN SERA
             (C) JOURNAL: LANCET
             (D) VOLUME: I
             (E) ISSUE:
             (F) PAGES: 72-73
             (G) DATE: 1975
             (H) DOCUMENT NUMBER:
             (I) FILING DATE:
             (J) PUBLICATION DATE:
             (K) RELEVANT RESIDUES IN SEQ ID NO: 14:

(xi) PUBLICATION INFORMATION:
             (A) AUTHORS: MANIATIS, T.
                          FRITSCH, E.F.
                          SAMBROOK, J.
             (B) TITLE: MOLECULAR CLONING
             (C) JOURNAL: COLD SPRING HARBOR, NY
             (D) VOLUME:
             (E) ISSUE:
             (F) PAGES:
             (G) DATE: 1982
             (H) DOCUMENT NUMBER:
             (I) FILING DATE:
             (J) PUBLICATION DATE:
             (K) RELEVANT RESIDUES IN SEQ ID NO: 14:

(xii) PUBLICATION INFORMATION:
             (A) AUTHORS: SMITH, D.B.
                          JOHNSON, K.S.
             (B) TITLE: SINGLE STEP PURIFICATION OF POLYPEPTIDES
                 EXPRESSED IN ESCHERICHIA COLI AS FUSIONS WITH
                 GLUTATHIONE S. TRANSFERASE
             (C) JOURNAL: GENE
             (D) VOLUME:
             (E) ISSUE: 67
             (F) PAGES: 31-40
             (G) DATE: 1988
             (H) DOCUMENT NUMBER:
             (I) FILING DATE:
             (J) PUBLICATION DATE:
             (K) RELEVANT RESIDUES IN SEQ ID NO: 14:

(xiii) SEQUENCE DESCRIPTION: SEQ ID NO: 14:

Met Thr Met Ile Thr Pro Ser Leu Ala Ala Glu Ala Ser Thr
1               5                   10

Gly Ala Gly Gly Gly Gly Ser Asn Ser Val Lys Ser Met Trp
15                  20                  25

Ser Glu Gly Ala Thr Phe Ser Ala Asn Ser Val Thr Cys Thr
    30                  35                  40

Phe Ser Arg Gln Phe Leu Ile Pro Tyr Asp Pro Glu His His
        45                  50                  55

Tyr Lys Val Phe Ser Pro Ala Ala Ser Ser Cys His Asn Ala
            60                  65                  70

Ser Gly Lys Glu Ala Lys Val Cys Thr Ile Ser Pro Ile Met

```
                    75                  80
Gly Tyr Ser Thr Pro Trp Arg Tyr Leu Asp Phe Asn Ala Leu
 85                  90                  95

Asn Leu Phe Phe Ser Pro Leu Glu Phe Gln His Leu Ile Glu
    100                 105                 110

Asn Tyr Gly Ser Ile Ala Pro Asp Ala Leu Thr Val Thr Ile
        115                 120                 125

Ser Glu Ile Ala Val Lys Asp Val Thr Asp Lys Thr Gly Gly
            130                 135                 140

Gly Val Gln Val Thr Asp Ser Thr Thr Gly Arg Leu Cys Met
                145                 150

Leu Val Asp His Glu Tyr Lys Tyr Pro Tyr Val Leu Gly Gln
155                 160                 165

Gly Gln Asp Thr Leu Ala Pro Glu Leu Pro Ile Trp Val Tyr
    170                 175                 180

Phe Pro Pro Gln Tyr Ala Tyr Leu Thr Val Gly Asp Val Asn
        185                 190                 195

Thr Gln Gly Ile Ser Gly Asp Ser Lys Lys Leu Ala Ser Glu
            200                 205                 210

Glu Ser Ala Phe Tyr Val Leu Glu His Ser Ser Phe Gln Leu
                215                 220

Leu Gly Thr Gly Gly Thr Ala Ser Met Ser Tyr Lys Phe Pro
225                 230                 235

Pro Val Pro Pro Glu Asn Leu Glu Gly Cys Arg Ser Thr Asp
    240                 245                 250

Pro Arg Glu Phe Thr Gly Arg Arg Phe Thr Thr Ser
        255                 260

(2) INFORMATION FOR SEQ ID NO: 15:

(i) SEQUENCE CHARACTERISTICS:
        (A) LENGTH: 227
        (B) TYPE: AMINO ACID
        (C) TOPOLOGY: LINEAR (ii) MOLECULE TYPE:
        (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
        INFECTION (ERYTHEMA INFECTIOSUM)

(vii) IMMEDIATE SOURCE: GENETICALLY ENGINEERED PEPTIDE (viii) POSITION IN GENOME: N/A (ix) FEATURE:
        (A) NAME/KEY: N/A
        (B) LOCATION: N/A
        (C) IDENTIFICATION METHOD: amino acid analysis and
            mass spectrometry
        (D) OTHER INFORMATION:

(x) PUBLICATION INFORMATION:
        (A) AUTHORS: COSSART, Y.E.
                     FIELD, A.M.
                     CANT, B.
                     WIDDOWS, D.
        (B) TITLE: PARVOVIRUS-LIKE PARTICLES IN HUMAN SERA
        (C) JOURNAL: LANCET
```

(D) VOLUME: I
                   (E) ISSUE:
                   (F) PAGES: 72-73
                   (G) DATE: 1975
                   (H) DOCUMENT NUMBER:
                   (I) FILING DATE:
                   (J) PUBLICATION DATE:
                   (K) RELEVANT RESIDUES IN SEQ ID NO: 15:

(xi) PUBLICATION INFORMATION:
                   (A) AUTHORS: MANIATIS, T.
                                FRITSCH, E.F.
                                SAMBROOK, J.
                   (B) TITLE: MOLECULAR CLONING
                   (C) JOURNAL: COLD SPRING HARBOR, NY
                   (D) VOLUME:
                   (E) ISSUE:
                   (F) PAGES:
                   (G) DATE: 1982
                   (H) DOCUMENT NUMBER:
                   (I) FILING DATE:
                   (J) PUBLICATION DATE:
                   (K) RELEVANT RESIDUES IN SEQ ID NO: 15:

(xii) PUBLICATION INFORMATION:
                   (A) AUTHORS: SMITH, D.B.
                                JOHNSON, K.S.
                   (B) TITLE: SINGLE STEP PURIFICATION OF POLYPEPTIDES
                       EXPRESSED IN ESCHERICHIA COLI AS FUSIONS WITH
                       GLUTATHIONE S. TRANSFERASE
                   (C) JOURNAL: GENE
                   (D) VOLUME:
                   (E) ISSUE: 67
                   (F) PAGES: 31-40
                   (G) DATE: 1988
                   (H) DOCUMENT NUMBER:
                   (I) FILING DATE:
                   (J) PUBLICATION DATE:
                   (K) RELEVANT RESIDUES IN SEQ ID NO: 15:

(xiii) SEQUENCE DESCRIPTION: SEQ ID NO: 15:

Met Ser Lys Lys Ser Gly Lys Trp Trp Glu Ser Asp Asp Lys
 1               5                  10

Phe Ala Lys Ala Val Tyr Gln Gln Phe Val Glu Phe Tyr Glu
15                  20                  25

Lys Val Thr Gly Thr Asp Leu Glu Leu Ile Gln Ile Leu Lys
        30                  35                  40

Asp His Tyr Asn Ile Ser Leu Asp Asn Pro Leu Glu Asn Pro
            45                  50                  55

Ser Ser Leu Phe Asp Leu Val Ala Arg Ile Lys Asn Asn Leu
                60                  65                  70

Lys Asn Ser Pro Asp Leu Tyr Ser His His Phe Gln Ser His
                    75                  80

Gly Gln Leu Ser Asp His Pro His Ala Leu Ser Ser Ser Ser
85                  90                  95

Ser His Ala Glu Pro Arg Gly Glu Asn Ala Val Leu Ser Ser
    100                 105                 110

Glu Asp Leu His Lys Pro Gly Gln Val Ser Val Gln Leu Pro
        115                 120                 125

Gly Thr Asn Tyr Val Gly Pro Gly Asn Glu Leu Gln Ala Gly
            130                 135                 140

Pro Pro Gln Ser Ala Val Asp Ser Ala Ala Arg Ile His Asp
                145                 150

Phe Arg Tyr Ser Gln Leu Ala Lys Leu Gly Ile Asn Pro Tyr
155                 160                 165

Thr His Trp Thr Val Ala Asp Glu Glu Leu Leu Lys Asn Ile

-continued

```
            170                 175                 180
Lys Asn Glu Thr Gly Phe Gln Ala Gln Val Val Lys Asp Tyr
        185                 190                 195

Phe Thr Leu Lys Gly Ala Ala Ala Pro Val Ala His Phe Gln
            200                 205                 210

Gly Ser Leu Pro Glu Val Pro Ala Tyr Asn Ala Ser Glu Lys
                215                 220

Tyr Pro Ser
225
```

(2) INFORMATION FOR SEQ ID NO: 16:

(i) SEQUENCE CHARACTERISTICS:
      (A) LENGTH: 500
      (B) TYPE: AMINO ACID
      (C) TOPOLOGY: LINEAR (ii) MOLECULE TYPE:
      (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
      INFECTION (ERYTHEMA INFECTIOSUM)

(vii) IMMEDIATE SOURCE: GENETICALLY ENGINEERED PEPTIDE (viii) POSITION IN GENOME: N/A (ix) FEATURE:
      (A) NAME/KEY: N/A
      (B) LOCATION: N/A
      (C) IDENTIFICATION METHOD: amino acid analysis and
          mass spectrometry
      (D) OTHER INFORMATION:

(x) PUBLICATION INFORMATION:
      (A) AUTHORS: COSSART, Y.E.
             FIELD, A.M.
             CANT, B.
             WIDDOWS, D.
      (B) TITLE: PARVOVIRUS-LIKE PARTICLES IN HUMAN SERA
      (C) JOURNAL: LANCET
      (D) VOLUME: I
      (E) ISSUE:
      (F) PAGES: 72-73
      (G) DATE: 1975
      (H) DOCUMENT NUMBER:
      (I) FILING DATE:
      (J) PUBLICATION DATE:
      (K) RELEVANT RESIDUES IN SEQ ID NO: 16:

(xi) PUBLICATION INFORMATION:
      (A) AUTHORS: MANIATIS, T.
             FRITSCH, E.F.
             SAMBROOK, J.
      (B) TITLE: MOLECULAR CLONING
      (C) JOURNAL: COLD SPRING HARBOR, NY
      (D) VOLUME:
      (E) ISSUE:
      (F) PAGES:
      (G) DATE: 1982
      (H) DOCUMENT NUMBER:
      (I) FILING DATE:
      (J) PUBLICATION DATE:
      (K) RELEVANT RESIDUES IN SEQ ID NO: 16:

(xii) PUBLICATION INFORMATION:
      (A) AUTHORS: SMITH, D.B.
             JOHNSON, K.S.

(B) TITLE: SINGLE STEP PURIFICATION OF POLYPEPTIDES
    EXPRESSED IN ESCHERICHIA COLI AS FUSIONS WITH
    GLUTATHIONE S. TRANSFERASE
(C) JOURNAL: GENE
(D) VOLUME:
(E) ISSUE: 67
(F) PAGES: 31-40
(G) DATE: 1988
(H) DOCUMENT NUMBER:
(I) FILING DATE:
(J) PUBLICATION DATE:
(K) RELEVANT RESIDUES IN SEQ ID NO: 16:

(xiii) SEQUENCE DESCRIPTION: SEQ ID NO: 16:

```
Met Thr Ile Thr Asn Ser Asp His Met Ser Lys Lys Ser Gly
1               5                   10

Lys Trp Trp Glu Ser Asp Lys Phe Ala Lys Ala Val Tyr
15                  20                  25

Gln Gln Phe Val Glu Phe Tyr Glu Lys Val Thr Gly Thr Asp
        30                  35                  40

Leu Glu Leu Ile Gln Ile Leu Lys Asp His Tyr Asn Ile Ser
            45                  50                  55

Leu Asp Asn Pro Leu Glu Asn Pro Ser Ser Leu Phe Asp Leu
                60                  65                  70

Val Ala Arg Ile Lys Asn Asn Leu Lys Asn Ser Pro Asp Leu
                75                  80

Tyr Ser His His Phe Gln Ser His Gly Gln Leu Ser Asp His
85              90                  95

Pro His Ala Leu Ser Ser Ser Ser His Ala Glu Pro Arg
    100                 105                 110

Gly Glu Asn Ala Val Leu Ser Ser Glu Asp Leu His Lys Pro
            115                 120                 125

Gly Gln Val Ser Val Gln Leu Pro Gly Thr Asn Tyr Val Gly
            130                 135                 140

Pro Gly Asn Glu Leu Gln Ala Gly Pro Pro Gln Ser Ala Val
                145                 150

Asp Ser Ala Ala Arg Ile His Asp Phe Arg Tyr Ser Gln Leu
155                 160                 165

Ala Lys Leu Gly Ile Asn Pro Tyr Thr His Trp Thr Val Ala
    170                 175                 180

Asp Glu Glu Leu Leu Lys Asn Ile Lys Asn Glu Thr Gly Phe
        185                 190                 195

Gln Ala Gln Val Val Lys Asp Tyr Phe Thr Leu Lys Gly Ala
            200                 205                 210

Ala Ala Pro Val Ala His Phe Gln Gly Ser Leu Pro Glu Val
                215                 220

Pro Ala Tyr Asn Ala Ser Glu Lys Tyr Pro Ser Met Thr Ser
225                 230                 235

Val Asn Ser Ala Glu Ala Ser Thr Gly Ala Gly Gly Gly Gly
    240                 245                 250

Ser Asn Ser Val Lys Ser Met Trp Ser Glu Gly Ala Thr Phe
        255                 260                 265

Ser Ala Asn Ser Val Thr Cys Thr Phe Ser Arg Gln Phe Leu
            270                 275                 280

Ile Pro Tyr Asp Pro Glu His His Tyr Lys Val Phe Ser Pro
                285                 290

Ala Ala Ser Ser Cys His Asn Ala Ser Gly Lys Glu Ala Lys
```

```
                  295                 300                 305
Val Cys Thr Ile Ser Pro Ile Met Gly Tyr Ser Thr Pro Trp
            310                 315                 320

Arg Tyr Leu Asp Phe Asn Ala Leu Asn Leu Phe Phe Ser Pro
            325                 330                 335

Leu Glu Phe Gln His Leu Ile Glu Asn Tyr Gly Ser Ile Ala
            340                 345                 350

Pro Asp Ala Leu Thr Val Thr Ile Ser Glu Ile Ala Val Lys
            355                 360

Asp Val Thr Asp Lys Thr Gly Gly Gly Val Gln Val Thr Asp
365                 370                 375

Ser Thr Thr Gly Arg Leu Cys Met Leu Val Asp His Glu Tyr
380                 385                 390

Lys Tyr Pro Tyr Val Leu Gly Gln Gly Gln Asp Thr Leu Ala
            395                 400                 405

Pro Glu Leu Pro Ile Trp Val Tyr Phe Pro Pro Gln Tyr Ala
            410                 415                 420

Tyr Leu Thr Val Gly Asp Val Asn Thr Gln Gly Ile Ser Gly
            425                 430

Asp Ser Lys Lys Leu Ala Ser Glu Glu Ser Ala Phe Tyr Val
435                 440                 445

Leu Glu His Ser Ser Phe Gln Leu Leu Gly Thr Gly Gly Thr
            450                 455                 460

Ala Ser Met Ser Tyr Lys Phe Pro Pro Val Pro Pro Glu Asn
            465                 470                 475

Leu Glu Gly Cys Ser Gln His Phe Tyr Glu Met Tyr Asn Pro
            480                 485                 490

Leu Tyr Gly Ser Ser Arg Val Asp Leu Gln
            495                 500

(2) INFORMATION FOR SEQ ID NO: 17:

(i) SEQUENCE CHARACTERISTICS:
        (A) LENGTH: 387
        (B) TYPE: AMINO ACID
        (C) TOPOLOGY: LINEAR (ii) MOLECULE TYPE:
        (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
         INFECTION (ERYTHEMA INFECTIOSUM)
         3700 MARKET STREET, PHILADELPHIA, PA  19104

(vii) IMMEDIATE SOURCE: GENETICALLY ENGINEERED PEPTIDE (viii) POSITION IN GENOME: N/A (ix) FEATURE:
         (A) NAME/KEY: N/A
         (B) LOCATION: N/A
         (C) IDENTIFICATION METHOD: amino acid analysis and
             mass spectrometry
         (D) OTHER INFORMATION:

(x) PUBLICATION INFORMATION:
        (A) AUTHORS: COSSART, Y.E.
                     FIELD, A.M.
```

CANT, B.
WIDDOWS, D.
(B) TITLE: PARVOVIRUS-LIKE PARTICLES IN HUMAN SERA
(C) JOURNAL: LANCET
(D) VOLUME: I
(E) ISSUE:
(F) PAGES: 72-73
(G) DATE: 1975
(H) DOCUMENT NUMBER:
(I) FILING DATE:
(J) PUBLICATION DATE:
(K) RELEVANT RESIDUES IN SEQ ID NO: 17:

(xi) PUBLICATION INFORMATION:
(A) AUTHORS: MANIATIS, T.
FRITSCH, E.F.
SAMBROOK, J.
(B) TITLE: MOLECULAR CLONING
(C) JOURNAL: COLD SPRING HARBOR, NY
(D) VOLUME:
(E) ISSUE:
(F) PAGES:
(G) DATE: 1982
(H) DOCUMENT NUMBER:
(I) FILING DATE:
(J) PUBLICATION DATE:
(K) RELEVANT RESIDUES IN SEQ ID NO: 15:

(xii) PUBLICATION INFORMATION:
(A) AUTHORS: SMITH, D.B.
JOHNSON, K.S.
(B) TITLE: SINGLE STEP PURIFICATION OF POLYPEPTIDES
EXPRESSED IN ESCHERICHIA COLI AS FUSIONS WITH
GLUTATHIONE S. TRANSFERASE
(C) JOURNAL: GENE
(D) VOLUME:
(E) ISSUE: 67
(F) PAGES: 31-40
(G) DATE: 1988
(H) DOCUMENT NUMBER:
(I) FILING DATE:
(J) PUBLICATION DATE:
(K) RELEVANT RESIDUES IN SEQ ID NO: 17:

(xiii) SEQUENCE DESCRIPTION: SEQ ID NO: 17:

```
Met Thr Ile Thr Asn Ser Asp His Met Ser Lys Lys Ser Gly
 1               5                  10

Lys Trp Trp Glu Ser Asp Asp Lys Phe Ala Lys Ala Val Tyr
15                  20                  25

Gln Gln Phe Val Glu Phe Tyr Glu Lys Val Thr Gly Thr Asp
        30                  35                  40

Leu Glu Leu Ile Gln Ile Leu Lys Asp His Tyr Asn Ile Ser
            45                  50                  55

Leu Asp Asn Pro Leu Glu Asn Pro Ser Ser Leu Phe Asp Leu
                60                  65                  70

Val Ala Arg Ile Lys Asn Asn Leu Lys Asn Ser Pro Asp Leu
                    75                  80

Tyr Ser His His Phe Gln Ser His Gly Gln Leu Ser Asp His
85                  90                  95

Pro His Ala Leu Ser Ser Ser Ser His Ala Glu Pro Arg
        100                 105                 110

Gly Glu Asn Ala Val Leu Ser Ser Glu Asp Leu His Lys Pro
            115                 120                 125

Gly Gln Val Ser Val Gln Leu Pro Gly Thr Asn Tyr Val Gly
                130                 135                 140

Pro Gly Asn Glu Leu Gln Ala Gly Pro Pro Gln Ser Ala Val
                    145                 150
```

```
Asp Ser Ala Ala Arg Ile His Asp Phe Arg Tyr Ser Gln Leu
155                 160                 165

Ala Lys Leu Gly Ile Asn Pro Tyr Thr His Trp Thr Val Ala
170                 175                 180

Asp Glu Glu Leu Leu Lys Asn Ile Lys Asn Glu Thr Gly Phe
            185                 190                 195

Gln Ala Gln Val Val Lys Asp Tyr Phe Thr Leu Lys Gly Ala
            200                 205                 210

Ala Ala Pro Val Ala His Phe Gln Gly Ser Leu Pro Glu Val
                    215                 220

Pro Ala Tyr Asn Ala Ser Glu Lys Tyr Pro Ser Met Thr Ser
225                 230                 235

Val Asn Ser Ala Glu Ala Ser Thr Gly Ala Gly Gly Gly Gly
    240                 245                 250

Ser Asn Ser Val Lys Ser Met Trp Ser Glu Gly Ala Thr Phe
    255                 260                 265

Ser Ala Asn Ser Val Thr Cys Thr Phe Ser Arg Gln Phe Leu
            270                 275                 280

Ile Pro Tyr Asp Pro Glu His His Tyr Lys Val Phe Ser Pro
            285                 290

Ala Ala Ser Ser Cys His Asn Ala Ser Gly Lys Glu Ala Lys
295                 300                 305

Val Cys Thr Ile Ser Pro Ile Met Gly Tyr Ser Thr Pro Trp
    310                 315                 320

Arg Tyr Leu Asp Phe Asn Ala Leu Asn Leu Phe Phe Ser Pro
            325                 330                 335

Leu Glu Phe Gln His Leu Ile Glu Asn Tyr Gly Ser Ile Ala
            340                 345                 350

Pro Asp Ala Leu Thr Val Thr Ile Ser Glu Ile Ala Val Lys
                    355                 360

Asp Val Thr Asp Lys Thr Gly Gly Gly Val Gln Val Thr Asp
365                 370                 375

Ser Thr Thr Gly Arg Leu Cys Ser Asn
    380                 385

(2) INFORMATION FOR SEQ ID NO: 18:

(i) SEQUENCE CHARACTERISTICS:
        (A) LENGTH: 501
        (B) TYPE: AMINO ACID
        (C) TOPOLOGY: LINEAR (ii) MOLECULE TYPE:
         (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
         INFECTION (ERYTHEMA INFECTIOSUM)
         3700 MARKET STREET, PHILADELPHIA, PA  19104

(vii) IMMEDIATE SOURCE: GENETICALLY ENGINEERED PEPTIDE (viii) POSITION IN GENOME: N/A (ix) FEATURE:
         (A) NAME/KEY: N/A
         (B) LOCATION: N/A
```

```
        (C) IDENTIFICATION METHOD: amino acid analysis and
            mass spectrometry
        (D) OTHER INFORMATION:

(x) PUBLICATION INFORMATION:
        (A) AUTHORS: COSSART, Y.E.
                     FIELD, A.M.
                     CANT, B.
                     WIDDOWS, D.
        (B) TITLE: PARVOVIRUS-LIKE PARTICLES IN HUMAN SERA
        (C) JOURNAL: LANCET
        (D) VOLUME: I
        (E) ISSUE:
        (F) PAGES: 72-73
        (G) DATE: 1975
        (H) DOCUMENT NUMBER:
        (I) FILING DATE:
        (J) PUBLICATION DATE:
        (K) RELEVANT RESIDUES IN SEQ ID NO: 18:

(xi) SEQUENCE DESCRIPTION: SEQ ID NO: 18:

Met Thr Met Ile Thr Asn Ser Asp His Met Ser Lys Lys Ser
1               5                   10

Gly Lys Trp Trp Glu Ser Asp Asp Lys Phe Ala Lys Ala Val
15                  20                  25

Tyr Gln Gln Phe Val Glu Phe Tyr Glu Lys Val Thr Gly Thr
    30                  35                  40

Asp Leu Glu Leu Ile Gln Ile Leu Lys Asp His Tyr Asn Ile
        45                  50                  55

Ser Leu Asp Asn Pro Leu Glu Asn Pro Ser Ser Leu Phe Asp
            60                  65                  70

Leu Val Ala Arg Ile Lys Asn Asn Leu Lys Asn Ser Pro Asp
                75                  80

Leu Tyr Ser His His Phe Gln Ser His Gly Gln Leu Ser Asp
85                  90                  95

His Pro His Ala Leu Ser Ser Ser Ser His Ala Glu Pro
        100                 105                 110

Arg Gly Glu Asn Ala Val Leu Ser Ser Glu Asp Leu His Lys
            115                 120                 125

Pro Gly Gln Val Ser Val Gln Leu Pro Gly Thr Asn Tyr Val
                130                 135                 140

Gly Pro Gly Asn Glu Leu Gln Ala Gly Pro Pro Gln Ser Ala
                145                 150

Val Asp Ser Ala Ala Arg Ile His Asp Phe Arg Tyr Ser Gln
155                 160                 165

Leu Ala Lys Leu Gly Ile Asn Pro Tyr Thr His Trp Thr Val
    170                 175                 180

Ala Asp Glu Glu Leu Leu Lys Asn Ile Lys Asn Glu Thr Gly
        185                 190                 195

Phe Gln Ala Gln Val Val Lys Asp Tyr Phe Thr Leu Lys Gly
            200                 205                 210

Ala Ala Ala Pro Val Ala His Phe Gln Gly Ser Leu Pro Glu
                215                 220

Val Pro Ala Tyr Asn Ala Ser Glu Lys Tyr Pro Ser Met Thr
225                 230                 235

Ser Val Asn Ser Ala Glu Ala Ser Thr Gly Ala Gly Gly Gly
    240                 245                 250

Gly Ser Asn Ser Val Lys Ser Met Trp Ser Glu Gly Ala Thr
        255                 260                 265
```

-continued

```
Phe Ser Ala Asn Ser Val Thr Cys Thr Phe Ser Arg Gln Phe
        270                 275                 280

Leu Ile Pro Tyr Asp Pro Glu His His Tyr Lys Val Phe Ser
        285                 290

Pro Ala Ala Ser Ser Cys His Asn Ala Ser Gly Lys Glu Ala
295                 300                 305

Lys Val Cys Thr Ile Ser Pro Ile Met Gly Tyr Ser Thr Pro
310                 315                 320

Trp Arg Tyr Leu Asp Phe Asn Ala Leu Asn Leu Phe Phe Ser
        325                 330                 335

Pro Leu Glu Phe Gln His Leu Ile Glu Asn Tyr Gly Ser Ile
        340                 345                 350

Ala Pro Asp Ala Leu Thr Val Thr Ile Ser Glu Ile Ala Val
            355                 360

Lys Asp Val Thr Asp Lys Thr Gly Gly Gly Val Gln Val Thr
365                 370                 375

Asp Ser Thr Thr Gly Arg Leu Cys Met Leu Val Asp His Glu
380                 385                 390

Tyr Lys Tyr Pro Tyr Val Leu Gly Gln Gly Gln Asp Thr Leu
        395                 400                 405

Ala Pro Glu Leu Pro Ile Trp Val Tyr Phe Pro Pro Gln Tyr
            410                 415                 420

Ala Tyr Leu Thr Val Gly Asp Val Asn Thr Gln Gly Ile Ser
            425                 430

Gly Asp Ser Lys Lys Leu Ala Ser Glu Glu Ser Ala Phe Tyr
435                 440                 445

Val Leu Glu His Ser Ser Phe Gln Leu Leu Gly Thr Gly Gly
        450                 455                 460

Thr Ala Ser Met Ser Tyr Lys Phe Pro Pro Val Pro Pro Glu
            465                 470                 475

Asn Leu Glu Gly Cys Ser Gln His Phe Tyr Glu Met Tyr Asn
                480                 485                 490

Pro Leu Tyr Gly Ser Ser Arg Val Asp Leu Gln
                495                 500
```

(2) INFORMATION FOR SEQ ID NO: 19:

(i) SEQUENCE CHARACTERISTICS:
        (A) LENGTH: 486
        (B) TYPE: AMINO ACID
        (C) TOPOLOGY: LINEAR (ii) MOLECULE TYPE:
        (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
       INFECTION (ERYTHEMA INFECTIOSUM)
       3700 MARKET STREET, PHILADELPHIA, PA 19104

(vii) IMMEDIATE SOURCE: GENETICALLY ENGINEERED PEPTIDE (viii) POSITION IN GENOME: N/A (ix) FEATURE:
        (A) NAME/KEY: N/A
        (B) LOCATION: N/A -continued

```
        (C) IDENTIFICATION METHOD: amino acid analysis and
            mass spectrometry
        (D) OTHER INFORMATION:

(x) PUBLICATION INFORMATION:
        (A) AUTHORS: COSSART, Y.E.
                     FIELD, A.M.
                     CANT, B.
                     WIDDOWS, D.
        (B) TITLE: PARVOVIRUS-LIKE PARTICLES IN HUMAN SERA
        (C) JOURNAL: LANCET
        (D) VOLUME: I
        (E) ISSUE:
        (F) PAGES: 72-73
        (G) DATE: 1975
        (H) DOCUMENT NUMBER:
        (I) FILING DATE:
        (J) PUBLICATION DATE:
        (K) RELEVANT RESIDUES IN SEQ ID NO: 19:

(xi) SEQUENCE DESCRIPTION: SEQ ID NO: 19:

Met Ser Lys Lys Ser Gly Lys Trp Trp Glu Ser Asp Asp Lys
1               5                   10

Phe Ala Lys Ala Val Tyr Gln Gln Phe Val Glu Phe Tyr Glu
15                  20                  25

Lys Val Thr Asp Thr Asp Leu Glu Leu Ile Gln Ile Leu Lys
        30              35                  40

Asp His Tyr Asn Ile Ser Leu Asp His Pro Leu Glu Asn Pro
            45                  50                  55

Ser Ser Leu Phe Asp Leu Val Ala Arg Ile Lys Asn Asn Leu
                60                  65                  70

Lys Asn Ser Pro Asp Leu Tyr Ser His His Phe Gln Ser His
                    75                  80

Gly Lys Leu Ser Asp His Pro His Ala Leu Ser Ser Ser Ser
85                  90                  95

Ser His Ala Glu Pro Arg Gly Glu Asn Ala Val Leu Ser Ser
        100                 105                 110

Gly Asp Leu His Lys Pro Gly Gln Val Ser Val Gln Leu Pro
            115                 120                 125

Gly Thr Asn Tyr Val Gly Pro Gly Asn Ile Leu Gln Ala Gly
                130                 135                 140

Pro Pro Gln Ser Ala Val Asp Ser Ala Ala Arg Ile His Asp
                    145                 150

Phe Arg Tyr Ser Gln Leu Ala Lys Leu Gly Ile Asn Pro Tyr
155                 160                 165

Thr His Trp Thr Val Ala Asp Glu Glu Leu Leu Lys Asn Ile
        170                 175                 180

Lys Asn Glu Thr Gly Phe Gln Ala Gln Val Val Lys Asp Tyr
            185                 190                 195

Phe Thr Leu Lys Gly Ala Ala Ala Pro Val Ala His Phe Gln
                200                 205                 210

Gly Ser Leu Pro Glu Val Pro Ala Tyr Asn Ala Ser Glu Lys
                    215                 220

Tyr Pro Ser Met Thr Ser Val Asn Ser Ala Glu Ala Ser Thr
225                 230                 235

Gly Ala Gly Gly Gly Ser Asn Pro Val Lys Ser Met Trp
        240                 245                 250

Ser Glu Gly Ala Thr Phe Ser Ala Asn Ser Val Thr Cys Thr
            255                 260                 265
```

```
Phe Ser Arg Gln Phe Leu Ile Pro Tyr Asp Pro Glu His His
            270                 275                 280

Tyr Lys Val Phe Ser Pro Ala Ala Ser Cys His Asn Ala
            285                 290

Ser Gly Lys Glu Ala Lys Val Cys Thr Ile Ser Pro Ile Met
295             300                 305

Gly Tyr Ser Thr Pro Trp Arg Tyr Leu Asp Phe Asn Ala Leu
            310                 315                 320

Asn Leu Phe Phe Ser Pro Leu Glu Phe Gln His Leu Ile Glu
            325                 330                 335

Asn Tyr Gly Ser Thr Ala Pro Asp Ala Leu Thr Val Thr Ile
            340                 345                 350

Ser Glu Ile Ala Val Lys Asp Val Thr Asp Lys Thr Gly Gly
            355                 360

Gly Val Gln Val Thr Asp Ser Ala Thr Gly Arg Leu Cys Met
365             370                 375

Leu Val Asp His Glu Tyr Lys Tyr Pro Tyr Val Leu Gly Gln
380             385                 390

Gly Gln Asp Thr Leu Ala Pro Glu Leu Pro Ile Trp Val Tyr
            395                 400                 405

Phe Pro Pro Gln Tyr Ala Tyr Leu Thr Val Gly Asp Val Asn
            410                 415                 420

Thr Gln Gly Ile Ser Gly Asp Ser Lys Lys Leu Ala Ser Glu
            425                 430

Glu Ser Ala Phe Tyr Val Leu Glu His Ser Ser Phe Gln Leu
435             440                 445

Leu Gly Thr Gly Gly Thr Ala Thr Met Ser Tyr Lys Phe Pro
            450                 455                 460

Pro Val Pro Pro Glu Asn Leu Glu Gly Cys Ser Gln His Phe
            465                 470                 475

Tyr Glu Met Tyr Asn Pro Leu Tyr Gly Ser
            480                 485
```

(2) INFORMATION FOR SEQ ID NO: 20:

(i) SEQUENCE CHARACTERISTICS:
        (A) LENGTH: 415
        (B) TYPE: AMINO ACID
        (C) TOPOLOGY: LINEAR (ii) MOLECULE TYPE:
        (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
        INFECTION (ERYTHEMA INFECTIOSUM)

(vii) IMMEDIATE SOURCE: GENETICALLY ENGINEERED PEPTIDE (viii) POSITION IN GENOME: N/A (ix) FEATURE:
        (A) NAME/KEY: N/A
        (B) LOCATION: N/A
        (C) IDENTIFICATION METHOD: amino acid analysis and
            mass spectrometry
        (D) OTHER INFORMATION:

-continued

```
    (x) PUBLICATION INFORMATION:
        (A) AUTHORS: COSSART, Y.E.
                     FIELD, A.M.
                     CANT, B.
                     WIDDOWS, D.
        (B) TITLE: PARVOVIRUS-LIKE PARTICLES IN HUMAN SERA
        (C) JOURNAL: LANCET
        (D) VOLUME: I
        (E) ISSUE:
        (F) PAGES: 72-73
        (G) DATE: 1975
        (H) DOCUMENT NUMBER:
        (I) FILING DATE:
        (J) PUBLICATION DATE:
        (K) RELEVANT RESIDUES IN SEQ ID NO: 20:

(xi) SEQUENCE DESCRIPTION: SEQ ID NO: 20:

Met Thr Met Ile Thr Pro Ser Leu His Ala Cys Met Leu Val
1               5                   10

Asp His Glu Tyr Lys Tyr Pro Tyr Val Leu Gly Gln Gly Gln
15              20                  25

Asp Thr Leu Ala Pro Glu Leu Pro Ile Trp Val Tyr Phe Pro
        30              35                  40

Pro Gln Tyr Ala Tyr Leu Thr Val Gly Asp Val Asn Thr Gly
            45              50                  55

Gly Ile Ser Gly Asp Ser Lys Lys Leu Ala Ser Glu Glu Ser
                60              65                  70

Ala Phe Tyr Val Leu Glu His Ser Ser Phe Gln Leu Leu Glu
                    75              80

Thr Gly Gly Thr Ala Ser Met Ser Tyr Lys Phe Pro Pro Val
85                  90                  95

Pro Pro Glu Asn Leu Glu Gly Cys Ser Gln His Phe Tyr Glu
    100                 105                 110

Met Tyr Asn Pro Leu Tyr Gly Ser Arg Leu Gly Val Pro Asp
        115                 120                 125

Thr Leu Gly Gly Asp Pro Lys Phe Arg Ser Leu Thr His Glu
            130                 135                 140

Asp His Ala Ile Gln Pro Gln Asn Phe Met Pro Gly Pro Leu
                145                 150

Val Asn Ser Val Ser Thr Lys Glu Gly Asp Ser Ser Asn Thr
155                 160                 165

Gly Ala Gly Lys Ala Leu Thr Gly Leu Ser Thr Gly Thr Ser
    170                 175                 180

Gln Asn Thr Arg Ile Ser Leu Arg Pro Gly Pro Val Ser Gln
        185                 190                 195

Pro Tyr His His Trp Asp Thr Asp Lys Tyr Val Thr Gly Ile
            200                 205                 210

Asn Ala Ile Ser His Gly Gln Thr Thr Tyr Gly Asn Ala Glu
                215                 220

Asp Lys Glu Tyr Gln Gln Gly Val Gly Arg Phe Pro Asn Glu
225                 230                 235

Lys Glu Gln Leu Lys Gln Leu Gln Gly Leu Asn Met His Thr
    240                 245                 250

Tyr Phe Pro Asn Lys Gly Thr Gln Gln Tyr Thr Asp Gln Ile
        255                 260                 265

Glu Arg Pro Leu Met Val Gly Ser Val Trp Asn Arg Arg Ala
            270                 275                 280

Leu His Tyr Glu Ser Gln Leu Trp Ser Lys Ile Pro Asn Leu
```

```
                        285                 290
Asp Asp Ser Phe Lys Thr Gln Phe Ala Ala Leu Gly Gly Trp
295                 300                 305

Gly Leu His Gln Pro Pro Gln Ile Phe Leu Lys Ile Leu
    310                 315                 320

Pro Glu Ser Gly Pro Ile Gly Gly Ile Lys Ser Met Gly Ile
                325                 330                 335

Thr Thr Leu Val Gln Tyr Ala Val Gly Ile Met Thr Val Thr
                340                 345                 350

Met Thr Phe Lys Leu Gly Pro Arg Lys Ala Thr Gly Arg Trp
                    355                 360

Asn Pro Gln Pro Gly Val Tyr Pro Pro His Ala Ala Gly His
365                 370                 375

Leu Pro Tyr Val Leu Tyr Asp Pro Thr Ala Thr Asp Ala Lys
    380                 385                 390

Gln His His Arg His Gly Tyr Glu Lys Pro Glu Glu Leu Trp
                395                 400                 405

Thr Ala Lys Ser Arg Val His Pro Leu
                410                 415

(2) INFORMATION FOR SEQ ID NO: 21:

(i) SEQUENCE CHARACTERISTICS:
        (A) LENGTH: 398
        (B) TYPE: AMINO ACID
        (C) TOPOLOGY: LINEAR (ii) MOLECULE TYPE:
        (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
         INFECTION (ERYTHEMA INFECTIOSUM)
         3700 MARKET STREET, PHILADELPHIA  19104

(vii) IMMEDIATE SOURCE: GENETICALLY ENGINEERED PEPTIDE (viii) POSITION IN GENOME: N/A (ix) FEATURE:
        (A) NAME/KEY: N/A
        (B) LOCATION: N/A
        (C) IDENTIFICATION METHOD: amino acid analysis and
            mass spectrometry
        (D) OTHER INFORMATION:

(x) PUBLICATION INFORMATION:
        (A) AUTHORS: COSSART, Y.E.
                     FIELD, A.M.
                     CANT, B.
                     WIDDOWS, D.
        (B) TITLE: PARVOVIRUS-LIKE PARTICLES IN HUMAN SERA
        (C) JOURNAL: LANCET
        (D) VOLUME: I
        (E) ISSUE:
        (F) PAGES: 72-73
        (G) DATE: 1975
        (H) DOCUMENT NUMBER:
        (I) FILING DATE:
        (J) PUBLICATION DATE:
        (K) RELEVANT RESIDUES IN SEQ ID NO: 21:

(xi) SEQUENCE DESCRIPTION: SEQ ID NO: 21:
```

-continued

```
Met Leu Val Asp His Glu Tyr Lys Tyr Pro Tyr Val Leu Gly
1               5                   10

Gln Gly Gln Asp Thr Leu Ala Pro Glu Leu Pro Ile Trp Val
15                  20                  25

Tyr Phe Pro Pro Gln Tyr Ala Tyr Leu Thr Val Gly Asp Val
        30                  35              40

Asn Thr Gln Gly Ile Ser Gly Asp Ser Lys Lys Leu Ala Ser
            45                  50                  55

Glu Glu Ser Ala Phe Tyr Val Leu Glu His Ser Ser Phe Gln
                60                  65                  70

Leu Leu Gly Thr Gly Gly Thr Ala Thr Met Ser Tyr Lys Phe
                    75                  80

Pro Pro Val Pro Pro Glu Asn Leu Glu Gly Cys Ser Gln His
85                      90                  95

Phe Tyr Glu Met Tyr Asn Pro Leu Tyr Gly Ser Arg Leu Gly
            100                 105                 110

Val Pro Asp Thr Leu Gly Gly Asp Pro Lys Phe Arg Ser Leu
                115                 120                 125

Thr His Glu Asp His Ala Ile Gln Pro Gln Asn Phe Met Pro
                130                 135                 140

Gly Pro Leu Val Asn Ser Val Ser Thr Lys Glu Gly Asp Ser
                    145                 150

Ser Asn Thr Gly Ala Gly Lys Ala Leu Thr Gly Leu Ser Thr
155                 160                 165

Gly Thr Ser Gln Asn Thr Arg Ile Ser Leu Arg Pro Gly Pro
    170                 175                 180

Val Ser Gln Pro Tyr His His Trp Asp Thr Asp Lys Tyr Val
        185                 190                 195

Thr Gly Ile Asn Ala Ile Ser His Gly Gln Thr Thr Tyr Gly
                200                 205                 210

Asn Ala Glu Asp Lys Glu Tyr Gln Gln Gly Val Gly Arg Phe
                    215                 220

Pro Asn Glu Lys Glu Gln Leu Lys Gln Leu Gln Gly Leu Asn
225                 230                 235

Met His Thr Tyr Phe Pro Asn Lys Gly Thr Gln Gln Tyr Thr
    240                 245                 250

Asp Gln Ile Glu Arg Pro Leu Met Val Gly Ser Val Trp Asn
        255                 260                 265

Arg Arg Ala Leu His Tyr Glu Ser Gln Leu Trp Ser Lys Ile
            270                 275                 280

Pro Asn Leu Asp Asp Ser Phe Lys Thr Gln Phe Ala Ala Leu
                285                 290

Gly Gly Trp Gly Leu His Gln Pro Pro Gln Ile Phe Lys
295                 300                 305

Tyr Tyr His Lys Val Gly Gln Leu Glu Val Leu Asn Gln Trp
    310                 315                 320

Glu Leu Leu Pro Phe Asn Met Pro Trp Glu Leu Gln Leu His
        325                 330                 335

Leu Asn Trp Gly Pro Val Lys Leu Gln Asp Gly Gly Ile Leu
            340                 345                 350

Asn Leu Glu Tyr Ile Pro Arg Thr Gln Gln Val Ile Tyr His
                355                 360

Met Tyr Tyr Met Thr Pro Gln Leu Gln Met Gln Asn Asn Thr
```

```
365                  370                  375
Thr Asp Met Asp Met Lys Ser Leu Lys Asn Cys Gly Gln Pro
    380                  385                  390

Lys Ala Val Cys Thr His
        395
```

(2) INFORMATION FOR SEQ ID NO: 22:

(i) SEQUENCE CHARACTERISTICS:
        (A) LENGTH: 543
        (B) TYPE: AMINO ACID
        (C) TOPOLOGY: LINEAR (ii) MOLECULE TYPE:
        (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: SERUM FROM PATIENT WITH ACUTE
        INFECTION (ERYTHEMA INFECTIOSUM)
        3700 MARKET STREET, PHILADELPHIA, PA  19104

(vii) IMMEDIATE SOURCE: GENETICALLY ENGINEERED PEPTIDE (viii) POSITION IN GENOME: N/A (ix) FEATURE:
        (A) NAME/KEY: N/A
        (B) LOCATION: N/A
        (C) IDENTIFICATION METHOD: amino acid analysis and
            mass spectrometry
        (D) OTHER INFORMATION:

(x) PUBLICATION INFORMATION:
        (A) AUTHORS: COSSART, Y.E.
                FIELD, A.M.
                CANT, B.
                WIDDOWS, D.
        (B) TITLE: PARVOVIRUS-LIKE PARTICLES IN HUMAN SERA
        (C) JOURNAL: LANCET
        (D) VOLUME: I
        (E) ISSUE:
        (F) PAGES: 72-73
        (G) DATE: 1975
        (H) DOCUMENT NUMBER:
        (I) FILING DATE:
        (J) PUBLICATION DATE:
        (K) RELEVANT RESIDUES IN SEQ ID NO: 22:

(xi) SEQUENCE DESCRIPTION: SEQ ID NO: 22:

```
Met Thr Met Ile Thr Asn Ser Leu Ile Met Thr Ser Val Asn
1                   5                   10

Ser Ala Glu Ala Ser Thr Gly Ala Gly Gly Gly Ser Asn
15                  20                  25

Ser Val Lys Ser Met Trp Ser Glu Gly Ala Thr Phe Ser Ala
    30                  35                  40

Asn Ser Val Thr Cys Thr Phe Ser Arg Gln Phe Leu Ile Pro
            45                  50                  55

Tyr Asp Pro Glu His His Tyr Lys Val Phe Ser Pro Ala Ala
                60                  65                  70

Ser Ser Cys His Asn Ala Ser Gly Lys Glu Ala Lys Val Cys
                75                  80

Thr Ile Ser Pro Ile Met Gly Tyr Ser Thr Pro Trp Arg Tyr
85                  90                  95
```

-continued

```
Leu Asp Phe Asn Ala Leu Asn Leu Phe Phe Ser Pro Leu Glu
        100                 105                 110

Phe Gln His Leu Ile Glu Asn Tyr Gly Ser Ile Ala Pro Asn
        115                 120                 125

Ala Leu Thr Val Thr Ile Ser Glu Ile Ala Val Lys Asp Val
        130                 135                 140

Thr Asp Lys Thr Gly Gly Val Gln Val Thr Asp Ser Thr
                145                 150

Thr Gly Arg Leu Cys Met Leu Val Asp His Glu Tyr Lys Tyr
155                 160                 165

Pro Tyr Val Leu Gly Gln Gly Gln Asp Thr Leu Ala Pro Glu
        170                 175                 180

Leu Pro Ile Trp Val Tyr Phe Pro Gln Tyr Ala Tyr Leu
        185                 190                 195

Thr Val Gly Asp Val Asn Thr Gln Gly Ile Ser Gly Asp Ser
                200                 205                 210

Lys Lys Leu Ala Ser Glu Glu Ser Ala Phe Tyr Val Leu Glu
                215                 220

His Ser Ser Phe Gln Leu Leu Gly Thr Gly Thr Ala Ser
225                 230                 235

Met Ser Tyr Lys Phe Pro Pro Val Pro Pro Glu Asn Leu Glu
        240                 245                 250

Gly Cys Ser Gln His Phe Tyr Glu Met Tyr Asn Pro Leu Tyr
                255                 260                 265

Gly Ser Arg Leu Gly Val Pro Asp Thr Leu Gly Gly Asp Pro
                270                 275                 280

Lys Phe Arg Ser Leu Thr His Glu Asp His Ala Ile Gln Pro
                285                 290

Gln Asn Phe Met Pro Gly Pro Leu Val Asn Ser Val Ser Thr
295                 300                 305

Lys Glu Gly Asp Ser Ser Asn Thr Gly Ala Gly Lys Ala Leu
        310                 315                 320

Thr Gly Leu Ser Thr Gly Thr Ser Gln Asn Thr Arg Ile Ser
        325                 330                 335

Leu Arg Pro Gly Pro Val Ser Gln Pro Tyr His His Trp Asp
                340                 345                 350

Thr Asp Lys Tyr Val Thr Gly Ile Asn Ala Ile Ser His Gly
                355                 360

Gln Thr Thr Tyr Gly Asn Ala Glu Asp Lys Glu Tyr Gln Gln
365                 370                 375

Gly Val Gly Arg Phe Pro Asn Glu Lys Glu Gln Leu Lys Gln
        380                 385                 390

Leu Gln Gly Leu Asn Met His Thr Tyr Phe Pro Asn Lys Gly
        395                 400                 405

Thr Gln Gln Tyr Thr Asp Gln Ile Glu Arg Pro Leu Met Val
                410                 415                 420

Gly Ser Val Trp Asn Arg Arg Ala Leu His Tyr Glu Ser Gln
                425                 430

Leu Trp Ser Lys Ile Pro Asn Leu Asp Asp Ser Phe Lys Thr
435                 440                 445

Gln Phe Ala Ala Leu Gly Gly Trp Gly Leu His Gln Pro Pro
        450                 455                 460

Pro Gln Ile Phe Leu Lys Gln Tyr Ala Val Gly Ile Met Thr
```

```
               465                 470                 475
Val Thr Met Thr Phe Lys Leu Gly Pro Arg Lys Ala Thr Gly
                480                 485                 490

Arg Trp Asn Pro Gln Pro Gly Val Tyr Pro Pro His Ala Ala
                495                 500

Gly His Leu Pro Tyr Val Leu Tyr Asp Pro Thr Ala Thr Asp
505                 510                 515

Ala Lys Gln His His Arg His Gly Tyr Glu Lys Pro Glu Glu
    520                 525                 530

Leu Trp Thr Ala Lys Ser Arg Val His Pro Leu
            535                 540
```

(2) INFORMATION FOR SEQ ID NO:23:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (xi) SEQUENCE DESCRIPTION: SEQ ID NO: 23:

```
ATGACCATGA TTACGATTTC GAGCTCGGTA CCCGGGGATG ATCCTCTAGA GTCGACCT        60

AGTAATTAAT TAGATCTCGA GCCCGCCTAA TGAGCGGGCT TTAAGCTT                  108
```

(2) INFORMATION FOR SEQ ID NO: 24:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 24:

```
GTGAATTCTG ATCATATGAG TAAAAGTAGT GGCAAATGG                             39
```

(2) INFORMATION FOR SEQ ID NO: 25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 25:

```
CTTCGGTCGT GACCACGTCC TCCCC                                            25
```

(2) INFORMATION FOR SEQ ID NO: 26:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO: 26:

```
GAGGAATTCT CTGATCATGA CTTCAGTTAA TTCTGCAGAA GCC                        43
```

(2) INFORMATION FOR SEQ ID NO: 27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear

```
    (xi) SEQUENCE DESCRIPTION: SEQ ID NO: 27:

GAGGGGTGGC ACGGGAGTCG GTCCTTCGAA GAG                                              33

(2) INFORMATION FOR SEQ ID NO: 28:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 28:

GGGCCCCCGC AAAG                                                                   14
```